US009392954B2

(12) United States Patent
Morita et al.

(10) Patent No.: US 9,392,954 B2
(45) Date of Patent: Jul. 19, 2016

(54) CLASSIFICATION ESTIMATING SYSTEM AND CLASSIFICATION ESTIMATING PROGRAM

(75) Inventors: Masahiko Morita, Ibaraki (JP); Hiroshi Kawata, Ibaraki (JP)

(73) Assignee: University of Tsukuba, Ibaraki (JP)

( * ) Notice: Subject to any disclaimer, the term of this patent is extended or adjusted under 35 U.S.C. 154(b) by 0 days.

(21) Appl. No.: 13/350,711

(22) Filed: Jan. 13, 2012

(65) Prior Publication Data

US 2012/0209134 A1    Aug. 16, 2012

Related U.S. Application Data

(63) Continuation of application No. PCT/JP2010/004585, filed on Jul. 14, 2010.

(30) Foreign Application Priority Data

Jul. 15, 2009    (JP) ................................ 2009-167222

(51) Int. Cl.
*A61B 5/04*    (2006.01)
*A61B 5/05*    (2006.01)
(Continued)

(52) U.S. Cl.
CPC ........... *A61B 5/0488* (2013.01); *A61B 5/04012* (2013.01); *A61B 5/6824* (2013.01); *A61B 5/7235* (2013.01); *A61B 5/7267* (2013.01);
(Continued)

(58) Field of Classification Search
CPC ........................................................ A61B 5/00
USPC ................................................. 600/546, 547
See application file for complete search history.

(56) References Cited

U.S. PATENT DOCUMENTS 5,505,208 A * 4/1996 Toomim et al. ............... 600/546
5,645,073 A * 7/1997 Kadefors et al. .............. 600/546
(Continued)

FOREIGN PATENT DOCUMENTS

JP    2005-011037    1/2005
JP    2009-064216    3/2009

OTHER PUBLICATIONS

Tomoyuki Shinbo, "Reinforcement Learning Using Selective Desensitization Neural Networks in the State Space with Redundant Dimensions," IEICE Technical Report, Jan. 12, 2009, vol. 108, No. 383, pp. 7 to 12.
(Continued)

*Primary Examiner* — Rene Towa
*Assistant Examiner* — May Abouelela
(74) *Attorney, Agent, or Firm* — Knobbe, Martens, Olson & Bear, LLP

(57) ABSTRACT

A classification estimating system can include an input element group; an intermediate element group into which are input values of first intermediate variables for which a first multiple desensitization, including an accumulation of values of each input element of a first input element group and each value of a first output sensitivity and each value of a first multiplex output sensitivity, has been carried out and calculated; an output element group into which is input a value of an output variable calculated based on a value of each intermediate element of a first intermediate element group and a value of each connection weight; a classification information estimating module for estimating classification information based on pre-stored correspondence relationship information and a value of the output variable; and a classification information display.

9 Claims, 14 Drawing Sheets

(51) Int. Cl.
*A61B 5/0488* (2006.01)
*A61B 5/00* (2006.01)
*G06K 9/00* (2006.01)
*G06N 99/00* (2010.01)
*G06F 3/01* (2006.01)

(52) U.S. Cl.
CPC ............... *G06F 3/015* (2013.01); *G06F 3/017* (2013.01); *G06K 9/00355* (2013.01); *G06N 99/005* (2013.01)

(56) References Cited

U.S. PATENT DOCUMENTS

| | | | |
|---|---|---|---|
| 6,440,067 B1* | 8/2002 | DeLuca et al. | 600/300 |
| 6,625,485 B2* | 9/2003 | Levendowski et al. | 600/544 |
| 6,965,842 B2* | 11/2005 | Rekimoto | 702/150 |
| 7,148,879 B2* | 12/2006 | Amento et al. | 345/158 |
| 7,359,750 B2* | 4/2008 | Song et al. | 600/547 |
| RE40,427 E* | 7/2008 | Nashner | 600/595 |
| 7,499,745 B2* | 3/2009 | Littrup et al. | 600/547 |
| 7,963,283 B2* | 6/2011 | Sinderby | 128/204.23 |
| 8,126,542 B2* | 2/2012 | Grey | 600/546 |
| 8,255,045 B2* | 8/2012 | Gharib et al. | 600/547 |
| 8,386,025 B2* | 2/2013 | Hoppe | 600/546 |
| 2004/0015096 A1* | 1/2004 | Mok et al. | 600/547 |
| 2004/0138583 A1* | 7/2004 | Galea | 600/547 |
| 2004/0167420 A1* | 8/2004 | Song et al. | 600/547 |
| 2005/0192488 A1* | 9/2005 | Bryenton et al. | 600/301 |
| 2005/0240087 A1* | 10/2005 | Keenan et al. | 600/301 |
| 2006/0071934 A1* | 4/2006 | Sagar et al. | 345/473 |
| 2006/0189882 A1* | 8/2006 | Thomas | 600/546 |
| 2006/0253174 A1* | 11/2006 | King | 607/62 |
| 2007/0060830 A1* | 3/2007 | Le et al. | 600/544 |
| 2007/0140562 A1* | 6/2007 | Linderman | 382/187 |
| 2008/0058668 A1* | 3/2008 | Seyed Momen et al. | 600/546 |
| 2008/0253695 A1* | 10/2008 | Sano et al. | 382/305 |
| 2009/0177297 A1* | 7/2009 | Yeh et al. | 700/85 |
| 2009/0326406 A1* | 12/2009 | Tan et al. | 600/546 |
| 2009/0327171 A1* | 12/2009 | Tan et al. | 706/12 |
| 2010/0145219 A1* | 6/2010 | Grey | 600/546 |
| 2011/0071417 A1* | 3/2011 | Liu et al. | 600/546 |
| 2011/0087128 A1* | 4/2011 | Sakoda et al. | 600/546 |
| 2011/0137196 A1* | 6/2011 | Kakei et al. | 600/546 |
| 2012/0245439 A1* | 9/2012 | Andre et al. | 600/310 |

OTHER PUBLICATIONS

Masahiko Morita, "Efficiency improvement of reinforce learning using a selective desensitization neural network," IEICE Technical Report, Mar. 5, 2008, vol. 107, No. 542, pp. 355 to 359.

Hiroshi Yokoi et al., "Now and Future of Cyborg Technology," The Society of Instrument and Control Engineers, Journal of the Society of Instrument and Control Engineers, vol. 47, Issue 4, pp. 351-358, Apr. 2008.

Masahiko Yoshikawa et al., "Real-Time Hand Motion Classification and Joint Angle Prediction Using EMG," The Institute of Electronics, Information and Communication Engineers (IEICE), Proceedings, vol. J92-D, No. 1, pp. 93-103, 2009.

Backpropagation, Kyushu Institute of Technology, obtained from the internet on May 15, 2009, Internet <URL:http://www.brain.kyutech.ac.jp/~furukawa/note/bp/bp.html>.

Fukuda Osamu et al., "An EMG-Controlled Ominidirectional Pointing Device." The Institute of Electronics, Information and Communication Engineers (IEICE), Proceedings, vol. J87-D-11, No. 10, pp. 1996-2003, Oct. 2004.

International Search Report of PCT Application No. PCT/JP2010/004585, filed Jul. 14, 2010.

Written Opinion of PCT Application No. PCT/JP2010/004585, filed Jul. 14, 2010.

* cited by examiner

Estimated time delay and classification rate
since building-up of motion

| | | [%] | | | | | |
|---|---|---|---|---|---|---|---|
| | | Set 1 | set 2 | set 3 | set 4 | set 5 | set 6 |
| 10 [ms] later | A | 0.00 | 27.08 | 0.00 | 0.00 | 26.39 | 0.00 |
| | B | 33.33 | 0.00 | 16.67 | 16.67 | 16.67 | 25.00 |
| | C | 22.42 | 0.00 | 0.00 | 0.00 | 0.00 | 33.33 |
| | D | 0.00 | 0.00 | 0.00 | 22.22 | 0.00 | 0.00 |
| | E | 0.00 | 0.00 | 0.00 | 0.00 | 0.00 | 0.00 |
| | F | 19.64 | 32.50 | 33.33 | 0.00 | 29.17 | 48.61 |
| 30 [ms] later | A | 25.46 | 26.56 | 25.00 | 33.33 | 42.78 | 33.33 |
| | B | 33.33 | 33.33 | 41.67 | 16.67 | 16.67 | 25.00 |
| | C | 41.49 | 45.60 | 64.81 | 68.40 | 0.00 | 33.33 |
| | D | 0.00 | 0.00 | 0.00 | 38.89 | 16.67 | 0.00 |
| | E | 0.00 | 0.00 | 30.56 | 0.00 | 31.25 | 0.00 |
| | F | 60.42 | 47.08 | 35.76 | 0.00 | 29.17 | 50.56 |
| 50 [ms] later | A | 26.11 | 58.19 | 57.78 | 33.33 | 40.81 | 32.87 |
| | B | 33.33 | 58.33 | 41.67 | 16.67 | 41.67 | 83.33 |
| | C | 21.53 | 43.33 | 87.50 | 69.65 | 16.20 | 50.00 |
| | D | 16.67 | 0.00 | 0.00 | 45.56 | 16.67 | 30.56 |
| | E | 33.33 | 0.00 | 47.92 | 32.29 | 57.41 | 23.61 |
| | F | 61.11 | 47.36 | 36.39 | 25.00 | 36.11 | 51.49 |
| 100 [ms] later | A | 77.10 | 88.89 | 57.41 | 33.33 | 70.28 | 63.89 |
| | B | 33.33 | 83.33 | 41.67 | 68.65 | 41.67 | 83.33 |
| | C | 59.17 | 42.22 | 60.56 | 54.30 | 55.34 | 83.14 |
| | D | 16.67 | 92.50 | 31.67 | 47.22 | 16.67 | 56.25 |
| | E | 82.64 | 81.25 | 84.10 | 59.95 | 57.99 | 85.93 |
| | F | 58.57 | 51.25 | 38.87 | 25.52 | 55.36 | 53.75 |
| 150 [ms] later | A | 77.36 | 88.86 | 82.14 | 66.25 | 73.26 | 63.89 |
| | B | 53.33 | 83.33 | 75.00 | 64.58 | 65.00 | 78.57 |
| | C | 61.94 | 42.50 | 82.64 | 41.01 | 56.76 | 80.83 |
| | D | 57.14 | 72.22 | 25.00 | 45.00 | 18.06 | 57.41 |
| | E | 87.82 | 81.19 | 81.22 | 59.26 | 78.11 | 87.08 |
| | F | 55.83 | 52.92 | 46.25 | 31.39 | 54.17 | 55.00 |

FIG. 15

CLASSIFICATION ESTIMATING SYSTEM AND CLASSIFICATION ESTIMATING PROGRAM

CROSS-REFERENCE TO RELATED APPLICATIONS

This application is a Continuation of International Application Number PCT/JP2010/004585, filed Jul. 14, 2010, which claims priority to Japanese Application No. 2009-167222, filed Jul. 15, 2009, the entire contents of both which are hereby incorporated by reference.

BACKGROUND OF THE INVENTIONS

1. Technical Field

The present inventions relate to a classification estimating system and classification estimating program through a selective desensitization neural network for estimating classification information including an operational decision of a subject.

2. Technical Background

In recent years, research and development on mechanical control using physiological information (biosignals) of human beings are overwhelmingly carried out. Said mechanical control is designed not only to provide assistance in power assistance to prosthetic arms and limbs, or self-help devices through assistive techniques and adaptive devices for those who are mobility challenged, but also to be expected for general application as control devices such as virtual reality devices and other human interface devices (as reflected in non-patent literature 1). In addition, said physiological information (biosignals) used in said mechanical control system comprises central nerve system information indicating change in brain wave and brain blood, and the nerve ending system information, which represents the EMG signals (muscle electrical signal, muscle action potential, EMG signals) indicating change of EMG signals (muscle potential signal, action potential) between said muscle and adjacent skin (as reflected in non-patent literature 1) that generate when muscle contracts.

It is known that said EMG signal can be observed 30-100 [ms] earlier than occurrence of said muscle contraction (as reflected in non-patent literature 2). That is to say, compared with said muscle contraction, said EMG signals can be measured with slight delay. Besides, the measuring device of said EMG signals has the features of high responsiveness (high sensitivity & response time) and high reliability of measured value, and can be provided at comparatively low cost. Hence application of said EMG signals, as physiological information, can be expected as practical and promising.

Here, two approaches are employed to measure said EMG signals, wherein the first approach applies needle electrodes that are sticked to muscle fiber on a subject (test subject, measured object) to obtain directly specific EMG signals; whereas the second approach applies electrodes (surface electrode) that are attached to skin of a subject to measure the combination of EMG signals generated by a plurality of muscle fibers, namely surface EMG signals (EMG: Electro Myo-Gram). Moreover, the approach that applies surface electrodes is preferable instead of the approach using said needle electrodes for it is regarded as less burdensome to a subject.

However, as combination of individual EMG signals, said surface EMG signals cause poor correspondence to motions (muscle action) of a subject due to their strong non-linear characteristic. In other words, it is difficult to classify said motions by means of said surface muscle EMG signals.

Therefore, in order to classify motions of a subject from the measured result of said surface EMG signals, neural net work techniques are applied to simplify a function (linear function) indicating the corresponding relationship between input and output based on distributed representation.

For example, motion classification techniques based on said surface EMG signals are described in the following non-patent literatures 1 and 2.

As shown in non-patent literatures 1, based on Back Propagation method (BP method) Multi-Layer Perceptron (MLP: Multi-Layered Perceptron), surface EMG signals obtained from three (3ch) electrodes (surface electrode and earth electrode) that attached to a subject's fore arm are input and 10 output fore arm motions are classified with an average recognition rate of 90%. Moreover, in non-patent literatures 1, it is described that surface EMG signals obtained from six (6ch) electrodes that are attached to a subject's wrist are input, and 6 kinds of output fore arm motion are classified with an average classification rate of 85%.

Said Multi-Layered Perceptron is a so called multi-layered neural network that the input, output as well as functions are expressed in distributed representation by elements (neutrons) comprising respectively an input layer, an intermediate layer and an output layer. With regard to said Multi-Layered Perceptron, each neuron of input and intermediate layer, each neuron of intermediate and output layer are connected respectively with connection weight, each neuron of intermediate layer as well as output layer are calculated as the sum of input from elements of input layer as well as intermediate layer by way of connection weight, in this way, said function is expressed as distributed representation. Moreover, Back Propagation method (BP method is a training algorithm to be used for the training of said perceptron, in which, when a set of training data namely a pair of input and output are given, the connection weight between each layer is modified in order for the output from Multi-Layered Perceptron to be correspondent to the output of training data. The detailed introduction of multi-layered perceptron based on Back Propagation method (BP method) is omitted for it has been described in not-patent literature 3.

In addition, LLGMN can as well be interpreted as a layer neutral network which comprises a statistical Gaussian Mixture Model and a probabilistic Hidden Markov Model. Besides, Gaussian mixture model is a probabilistic model that assumes linear combination of Gaussian distribution (normal distribution). Moreover, Markov Model is a stochastic process in which the occurrence probability of a current symbol depends on its immediate preceding n symbols, that is to say, Markov Model is a stochastic model in which it is assumed that the occurrence of a symbol depends on Markov process (a stochastic process having Markov property). Also, Hidden Markov Model is assumed to be a Markov process of system with unknown Parameters that estimates unknown parameters from observable information.

R-LLGMN is a LLGMN having possible connection of output between the first intermediate layer and the second intermediate layer at previous time step, namely recurrent connection. Also, the detailed explanation of R-LLGMN is omitted for it is described in Kokai publication Patent Tokukai No. 2005-11037 and non-patent literature 4.

As described in non-patent literatures 2, by means of Support Vector Machine, seven motions of fore arm (neutral, wrist flexion, wrist extension, grasp, open, wrist pronation, wrist supination) can be classified by inputting surface EMG signals based on measurement of EMG signals obtained from four channel electrodes attached on fore arm of a subject. In addition, as shown in non-patent literatures 2, seven motions of fore arm are classified with an average classification rate of 93.3%.

Here, said Support Vector Machine refers to a two class pattern classifier using a plurality of linear input elements (perceptron) as elements of the input layer. That is to say, it is a layer neutral network where the output values are determined by whether or not the sum of a plurality of linear input elements, multiplied by its respective connection weight (synaptic weight), exceeds a preset threshold value and then output values are output.

More specifically, let x ($x=(x_1, x_2, \ldots, x_n)$) denote the value set of n elements of input layer (input value) as input feature property vector, y denote the value of one element of the output layer (output value), $\omega$ ($\omega=(\omega_1, \omega_2, \ldots, \omega_n)$) denote the vector of the connection weight (connection weight vector) of each input element as well as the output element, $\omega^T$ denote the transpose vector of connection weight vector $\omega$, and h denote the threshold value, then the output value y can be defined as expressed in the following function (1).

$$y = \text{sign}(\omega^T x - h)$$
$$= \text{sign}(x_1\omega_1 + x_2\omega_2 + \ldots + x_n\omega_n - h)$$

equation (1)

Besides, sign($\omega^1$x-h) is a matrix sign function which takes the value +1 when ($\omega^T$X-h)>0, and −1 when ($\omega^T$x-h)≤0. That is to say, the inner product of vector x, and $\omega$ is a two value function which takes the value +1 when it exceeds threshold value h, and −1 when it does not exceed threshold value h.

In addition, said Support Vector Machine is a training machine that helps to train parameters of said linear input elements, that is to say, to update connection weight vector $\omega$ based on maximum margin criterion in order to find the separating surface (hyperplane) that has the largest distance between each data points, namely between input feature vector x (magin) by means of training data (training sample), namely a pair of input feature vector x as well as output value y.

DESCRIPTION OF THE RELATED ART

Non-patent literature 1: Hiroshi yokoi and one other, Now and Future of Cyborg Technology, The Society of Instrument and Control Engineers, Journal of the Society of Instrument and Control Engineers, Vol. 47, Issue. 4, pp. 93-103, April 2008

Non-patent literature 2: Masahiro Yoshikawa and three others, Real-Time Hand Motion Classification and Joint Angle Prediction Using EMG "The Institute of Electronics, Information and Communication Engineers (IEICE), Proceedings, vol. J92-D, No. 1, pp. 93-103, 2009

Non-patent literature 3: Backpropagation, Kyushu Institute of Technology, obtained from the internet on May 15, 2009, Internet, <URL: http://www.brain.kyutech.ac.jp/~furukawa/note/bp/bp.html>

Non-patent literature 4: Fukuda Osamu and two others, An EMG-Controlled Omnidirectional Pointing Device. The Institute of Electronics, Information and Communication Engineers (IEICE), Proceedings, vol. J87-D-☐, No. 10, pp. 1996-2003, October 2004

SUMMARY OF THE INVENTIONS

In said techniques described in non-patent literatures 1 and 2, motion classification of neutral position, neutral, wrist flexion, wrist extension, grasp, open, wrist pronation, wrist supination etc on fore wrist was carried out on the condition that the same motion was carried out at a constant velocity model. Thus, with said techniques described in non-patent literatures 1 and 2, there exists a problem that motion classification is impossible when different velocity models are concerned.

Additionally, while there are variations among the individual subject's performance, in order to perform motion classification with high classification accuracy, a specific individual subject is required to study training data samples, and also the determination of specific connection weights corresponding to individual subjects is deemed necessary; whereas regarding to unspecific plural subjects, it is required to study a plurality of training data samples and also universally applicable connection weights are required to be determined. In other words, the techniques described in said non-patent literatures 1 and 2 are applied to perform motion classification based on statistic approach to result in the necessity of a plurality of training data samples, which furthermore causes it burdensome to a subject hence to be deemed as impractical.

Additionally, as shown in said non-patent literatures 1 and 2, in order to perform classification for more motions and furtherly classification for motion velocities as well, it is necessary to carry out complicated feature extraction aiming at extracting motion features such as motion type and velocity. Accordingly, it is difficult to carry out real-time classification for complicated motions by means of the techniques described in said non-patent literatures 1 and 2.

Consequently, with techniques described in said non-patent literatures 1 and 2, it is difficult to carry out real-time classification for a plurality of motions together with motion velocities at high classification rate with little training data (training, sample data).

Therefore, on the basis of the problems described in the prior art, the subject of the present invention is to firstly solve the technical problems to enable motion classification of a subject with little training involved; secondly, to estimate classification information including an operational decision of a subject with little training.

The classification estimating system described in the present invention according to claim 1 in order to solve the above-mentioned technical problems, wherein the classification estimation system comprises:

An input element group comprising a first input element group comprising a plurality of input elements into which are input values of the first input variable based on a first information, the discrete values into which are input values of the first input variable, the input element group comprising a combination pattern of the discrete values based on a first information and a second input element group consisted of a plurality of input elements into which are input values of the second input variable based on a second information, the discrete values into which are input values of the second input variable, the input element group comprising a combination pattern of the discrete values based on the second information;

An intermediate element group provided with a first intermediate element group comprising a plurality of intermediate elements into which are input a first intermediate variables which are calculated from the value of each input element of said first input element group, wherein a first multiple desensitization including at least a product of each value of a first output sensitivity and each value of a first multiplex output sensitivity has been carried out while some values become zero; wherein each value of the first output sensitivity is calculated according to each value of input element of said first input element group and each value of input element of said second input element group in order for some values to become zero, and the remaining values become discrete values other than zero and each value of the first multiplex output sensitivity is calculated according to each pre-set value of the element of the multiplex element group in order for some values to become zero;

An output element group comprising a plurality of output elements into which are input the values of output variables which the values of output variables are zero or discrete values other than zero are calculated according to each value of said intermediate element of first intermediate variables and each pre-set value of connection weights corresponding to the importance of each value of said immediate elements;

A correspondence relationship information memorizing means to memorize correspondence relationship information, which specifies the correspondence relationship between a plurality of classification information, as the object of classification, and the combination pattern of the values of said a plurality of output elements which comprise an output element group are zero or discrete values other than zero, corresponding to the classification information;

A classification information estimating means to estimate said classification information corresponding to said first and second information that are input according to said correspondence relationship information pre-stored in said correspondence relationship information memorizing means and the calculated combination pattern of values of said plurality of output elements are zero or discrete values other than zero;

A classification information display means to display said classification information that is estimated according to said classification information estimating means.

The invention described in claim 2 referring to a classification estimating system according to claim 1, wherein the classification estimating system comprises:

Said intermediate element group provided with a second intermediate element group comprising a plurality of intermediate elements into which are input a second intermediate variables which are calculated from the values of each input element of said second input element group, wherein a second multiple desensitization including at least a product of each value of a second output sensitivity and each value of a second multiplex output sensitivity has been carried out while some values become zero, and the remaining values are become discrete values other than zero; wherein each value of the second output sensitivity is calculated according to each value of input element of said first input element group and each value of input elements of said second input element group in order for some values to become zero, and the remaining values are become discrete values other than zero and each value of the first multiplex output sensitivity is calculated according to each pre-set value of the elements of a plurality of element group in order for some values to become zero;

Said output element group into which are input the values of output variables which are calculated according to each value of the elements of said intermediate variables and each pre-set value of connection weights corresponding to the importance of each value of said immediate elements.

The invention described in claim 3 referring to a classification estimating system according to any one of claim 1 or 2, comprising:

Said classification information estimated according to said classification information estimating means; A connection weight training means to study each value of said connection weights by way of updating each value of said connection weights based on the difference from the real classification information extracted from said input first and second information.

The invention described in claim 4 referring to a classification estimating system according to any one of claims 1 to 3, wherein:

Each value of element of said multiplex element group is calculated according to said first and second information.

The invention described in claim 5 referring to a classification estimating system according to any one of claims 1 to 4, wherein the classification estimating system comprises:

Measuring devices comprising a first measuring device which measures said biosignals at the first measuring section arranged on said subject; and a second measuring device which measures said biosignals at the second measuring section arranged on said subject which is different from the first measuring section, wherein said classification information is taken as the operational decision of a subject and together with said operational decision, said first as well as the second information is taken as the biosignals of said subject.

The invention described in claim 6 referring to a classification estimating system according to claim 5, wherein the classification estimating system comprises:

Said measuring devices comprising said first measuring device which measures said surface EMG signals at said first measuring section arranged on said skin; and said second measuring device which measures said surface EMG signals at said second measuring section arranged on said skin, wherein among the EMG signals indicating the information on potential change based on the muscle activity of the muscle group of said subject, together with said operational decision, said EMG signals measured at the skin of said subject are taken as said surface EMG signals, whereas said EMG signals are taken as the surface EMG signals;

An integrated value calculating method for calculating the integrated values of said surface EMG signals measured by said first measuring device as the first integrated value, as well as the integrated values of said surface EMG signals measured by said second measuring device as the second integrated values;

An average integrated value calculating method for calculating the average values of the first integrated values as the first average integrated values over a certain preset shift time, as well as the average values of the second integrated values as the second average integrated value over said shift time within a certain pre-set time frame;

Said input element group comprising said first input element group into which are input the values of said first input variable over said shift time according to said first average integrated value, and said second input element group into which are input the values of said second input variable over said shift time according to said second average integrated value, wherein said first information is taken as said first average integrated value and said second information is taken as said second average integrated value;

The invention described in claim 7 referring to a classification estimating system according to claim 5 or 6 comprising:

Said classification information estimating means to estimate said classification information including, information on types to specify the information of motion types according to said operational decision, as well as information on force as the information of force of said motions.

The invention described in claim 8 referring to a classification estimating system according to claim 7, wherein the classification estimating system comprises:

Said classification information estimating means to estimate said classification information comprising said velocity information which, as velocity information, is the information on velocity of said motion, based on said force information on types to specify the information of motion types according to said operational decision, and the information on force as the information of force of said motions.

The invention described in claim 9 referring to a classification estimating system according to claim 8, wherein the classification estimating system comprises:

Said output element group comprising the first output element group consisting of a plurality of output elements into which are input the values of the first output variables corresponding to the first operational decision and the second output element group consisting of a plurality of output elements into which are input the values of the second output variables corresponding to the second operational decision among the values of said output variables;

Said correspondence relationship information memorizing means to memorize said correspondence relationship information which specifies the correspondence relationship between said information on types of said first operational decision as well as said velocity information, and the value of said first output variables; and the correspondence relationship between said information on types of said second operational decision as well as said velocity information, and the value of said second output variables;

Said classification information estimating means to estimate said type information of said classification information as well as said velocity information according to said first and second information into which are input the values based on said correspondence relationship information memorized in said correspondence relationship memorizing means as well as the calculated values of said first output variables and said second output variables;

Said classification information estimating means to indicate said type information of said classification information; as well as said velocity information according to said classification information estimating means.

The classification estimating program described in claim 10 in order to solve the above-mentioned technical problems, wherein a computer is functioned as:

An input value memorizing means which memorize the values of said first input variables as well as the values of said second input variables with regard to the input element group which comprises a first input element group derived from a plurality of input elements into which are input values of the first input variables based on the first information, the discrete values into which are input values of the first input variable, the input element group comprising a combination pattern of the discrete values based on a first information; a second input element group derived from a plurality of input elements into which are input values of the second input variables based on the first information, the discrete values into which are input values of the second input variable, the input element group comprising a combination pattern of the discrete values based on a second information;

An intermediate value calculating means to calculate the values of said first intermediate variables with regard to the intermediate element group provided with a first intermediate element group which comprises a plurality of intermediate elements into which are input a first intermediate variables which are calculated from the value of each input element of said first input element group, for which a first multiple desensitization including at least a product of each value of a first output sensitivity and each value of a first multiplex output sensitivity has been carried out while some values become zero; wherein each value of a first output sensitivity is calculated according to each value of input element of said first input element group and each value of input element of said second input element group in order for some values to become zero, and the remaining values become discrete values other than zero and each value of a first multiplex output sensitivity is calculated according to each pre-set value of the element of the multiplex element group in order for some values to become zero;

An output calculating means to calculate the values of said output variables regarding the output element group comprising a plurality of output elements into which are input the values of output variables which the values of output variables are zero or discrete values other than zero are calculated according to each value of said intermediate element of first intermediate variables and each pre-set value of connection weights corresponding to the importance of each value of said immediate elements;

A correspondence relationship information memorizing means to memorize correspondence relationship information which specifies the correspondence relationship between the multiple classification information as the object of classification; and the combination pattern of the values of said a plurality of output elements which comprise an output element group are zero or discrete values other than zero, corresponding to the classification information;

A classification information estimating means to estimate said classification information corresponding to said first and second information that are input based on said correspondence relationship information pre-stored in said correspondence relationship information memorizing means and the calculated combination pattern of values of said a plurality of output elements are zero or discrete values other than zero;

A classification information display means to display said classification information estimated according to said classification information estimating means.

According to the invention described in claims 1 and 10, it is possible to estimate the classification information by way of inputting each value of the input variables based on the first and second information into the selective desensitization neutral network that enables multiple desensitization, and classification information is estimated through said selective desensitization neutral network with high training ability (generalization ability); therefore, compared with the classification information estimation where the selective desensitization neutral network that enables multiple desensitization is not applied, classification information estimation can be carried out with less learning requirement.

According to the invention described in claim 2, motion classification of a subject is carried out through an mutual modification model of the selective desensitization neutral network that enables multiple desensitization, therefore the values of two input variables are modified mutually (Multiple Mutually Desensitized) to make it possible for the calculation of two intermediate variables; which hence results in an improved training ability for the selective desensitization neutral network that enables successful multiple desensitization with high classification rate in estimating classification information compared with the case when the values of two input variables are modified through product-type modification (where only one value being desensitized).

According to the invention described in claim 3, the values of the output variables can be calculated and classification information can be estimated with comparatively high classification rate based on each value of trained connection weights.

According to the invention described in claim 4, compared with each calculated value of the elements of multiple element group based on the first or second information, each calculated value of the element of multiple element group based on the first and second information tends to be with high possibility, different from each value of the element of multiple element group based on the first or second information; the values of desensitized input elements tend to be difficult to deviate, which results in a high training ability for the selective desensitization neutral network that enables multiple desensitization and successful estimation of classification with comparatively high classification rate.

According to the invention described in claim 5, the operational decision of a subject can be estimated through selective desensitization neutral network that enables multiple desensitization of each value of the input variables based on biosignals. In addition, according to the invention described in claim 5, motion classification of a subject can be carried out while a subject performs corresponding motions according to said operational decision.

According to the invention described in claim 6, the operational decision of a subject can be estimated by inputting the values of the input variables based on the calculated average integrated value of the surface EMG signal per shift time into the selective desensitization neutral network. Compared with the case when inputting the values of the input variables directly based on the value of the surface EMG signal and its integrated value as biosignals, the interference caused by noise of surface EMG signal can be reduced. Moreover, according to the invention described in claim 6, the change of surface EMG signals accompanying the motions of a subject is detected 30 [ms]~100 [ms] earlier than the muscle contraction accompanying the motions of a subject, hence, shift time can be decided to be shorter than the pre-set 30 [ms] resulting in a successful real time motion classification of a subject.

According to the invention described in claim 7, motion type and force can be estimated while estimating operational decision of a subject.

According to the invention described in claim 8, motion velocity and force can be estimated while estimating operational decision of a subject.

According to the invention described in claim 9, comparison between values of the first output variables corresponding to the first operational decision and values of the second output variables corresponding to the second operational decision can be carried out to estimate motion type and velocity.

BRIEF DESCRIPTION OF THE DRAWINGS

FIG. 11A illustrates the correct classification values for six motions that are actually performed;

FIG. 11B indicates the unsmoothed measured classification values for six motions that are actually performed against time frame;

FIG. 11C illustrates the smoothed measured classification values for six motions that are actually performed against time frame;

FIG. 15 illustrates the experimental results in experiment 1 of the change of time delay for estimation from starting of a motion by the changing of classification rate with time; as shown in the table for different sets of motions, it indicates the change of classification rate at three velocities for six types of motions after a certain period time from the start of motion.

Figure 1:
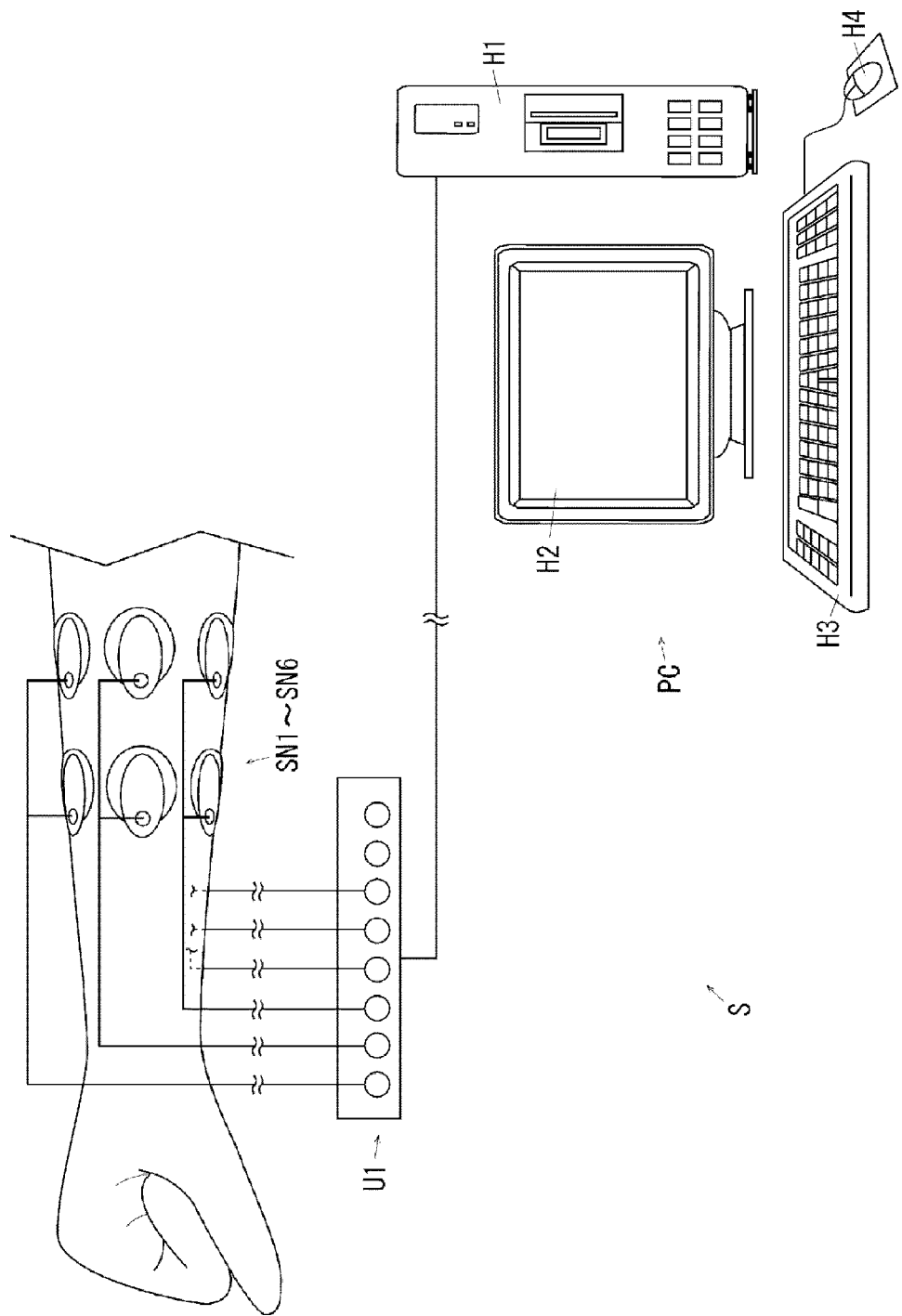
FIG. 1 is a schematic diagram illustrating the motion classification system in embodiment 1 of the present invention.

EXPLANATION OF SYMBOLS $\omega_{rij}^{\mu,\nu}$ ... value of connection weight, AP1 ... type estimating program, C1 ... integrated value calculating means, C5 ... average integrated value calculating means, C13 ... input value memorizing means, C15 intermediate value calculating means, C17 ... output value calculating means, C19 ... correspondence relationship information memorizing means, C20 ... classification information estimating means, C21 ... classification information display means, C23 ... connection weight training means, $G_1^1$~$G_8^1$, $G_i^1$, Na ... input element group, $G_1^1$ ... the first input element group, $G_2^1$ ... the second input element group, $G_8^1$ ... the multiplex element group, $G_{1,2}^2$~$G_{7,6}^2$, $G_{\mu,\nu}^2$, Nb ... intermediate element group, $G_{1,2}^2$~the first intermediate element group, $G_{2,1}^2$~the second intermediate element group, $G_1^3 G_6^3, G_r^3$, Nc ... output element group, $G_1^3$ ... the first output element group, $G_2^3$ ... the second output element group, $g_1^{\mu,\nu}$~$g_{30}^{\mu,\nu}$, $g_j^{\mu,\nu}$, $g_1^{\mu,\nu,8}$~$g_{30}^{\mu,\nu,8}$, $g_k^{\mu,\nu,8}$ ... values of output sensitivity, $g_1^{1,2}$~$g_{30}^{1,2}$, $g_j^{1,2}$ ... values of the first output sensitivity, $g_1^{2,1}$~$g_{30}^{2,1}$, $g_j^{2,1}$ ... values of the second output sensitivity, $g_1^{1,2,8}$~$g_{30}^{1,2,8}$, $g_k^{1,2,8}$ ... values of the first multiplex output sensitivity, $g_1^{2,1,8}$~$g_{30}^{2,1,8}$, $g_k^{2,1,8}$ ... values of the second multiplex output sensitivity, $N_i(p)$, $N_a(p)$, $N_d(p)$, $(x_1^i, x_2^i, \ldots x_{30}^i)$ ... values of input variables, $N_1(p)$, $(x_1^1, x_2^1, \ldots x_{30}^1)$ ... values of the first input variables, $N_2(p)$, $(x_1^2, x_2^2, \ldots x_{30}^2)$ ... values of the second input variables, PC ... computer, S ... classification estimating system, SN1~SN6 ... measuring devices, SN1 ... the first measuring device, SN2 ... the second measuring device, $s_1$ ... the first integrated value, $s_2$ ... the second integrated value, T ... correspondence relationship information, U1 ... measuring apparatus, $v_1$ ... the first average integrated value, $v_2$ ... the second average integrated value, $x_1$~$x_8$, $x_i$ ... input variables, $x_1$ ... the first input variables, $x_2$ ... the second input variables, $x_1^\mu$~$x_{30}^\mu$, $x_1^1$~$x_{30}^1$, $x_i^1$, $x_j^1$ ... value of each input element of the first input element group, $x_1^2$~$x_{30}^2$, $x_i^2$, $x_j^2$ ... value of each input element of the second input element group, $x_1^8$~$x_{30}^8$, $x_k^8$ ... value of each element of multiplex element group, $x_{1,2}$~$x_{7,6}$, $x_{\mu,\nu}$ ... Intermediate variables, $x_{1,2}$ ... the first intermediate variables, $x_{2,1}$ ... element group, $x_1^{\mu,\nu}$~$x_{30}^{\mu,\nu}$, $x_i^{\mu,\nu}$, $x_j^{\mu,\nu}$ ... values of each intermediate element of the second intermediate element group, $(x_1^{\mu,\nu}, x_2^{\mu,\nu}, \ldots, x_{30}^{\mu,\nu})$ ... values of the intermediate variables, $(x_1^{1,2}, x_2^{1,2}, \ldots x_{30}^{1,2})$ ... values of the first intermediate variables, $(x_1^{2,1}, x_2^{2,1}, \ldots x_{30}^{2,1})$ ... values of the second intermediate variables, $y_1$~$y_6$, $y_Y$ ... output variables, $y_i^Y$ ... values of output variables.

DETAILED DESCRIPTION OF THE PREFERRED EMBODIMENTS

Hereinafter, a preferred embodiment of the present invention will be described in detail with reference to the accompanying drawings, it should be noted the preferred embodiment(s) is merely exemplary in nature and is in no way intended to limit the invention.

In addition, in order for a better understanding, some drawings except the necessary ones are omitted in the following description.

Embodiment 1

FIG. 1 is a schematic diagram illustrating the motion classification system in embodiment 1 of the present invention.

Figure 2:
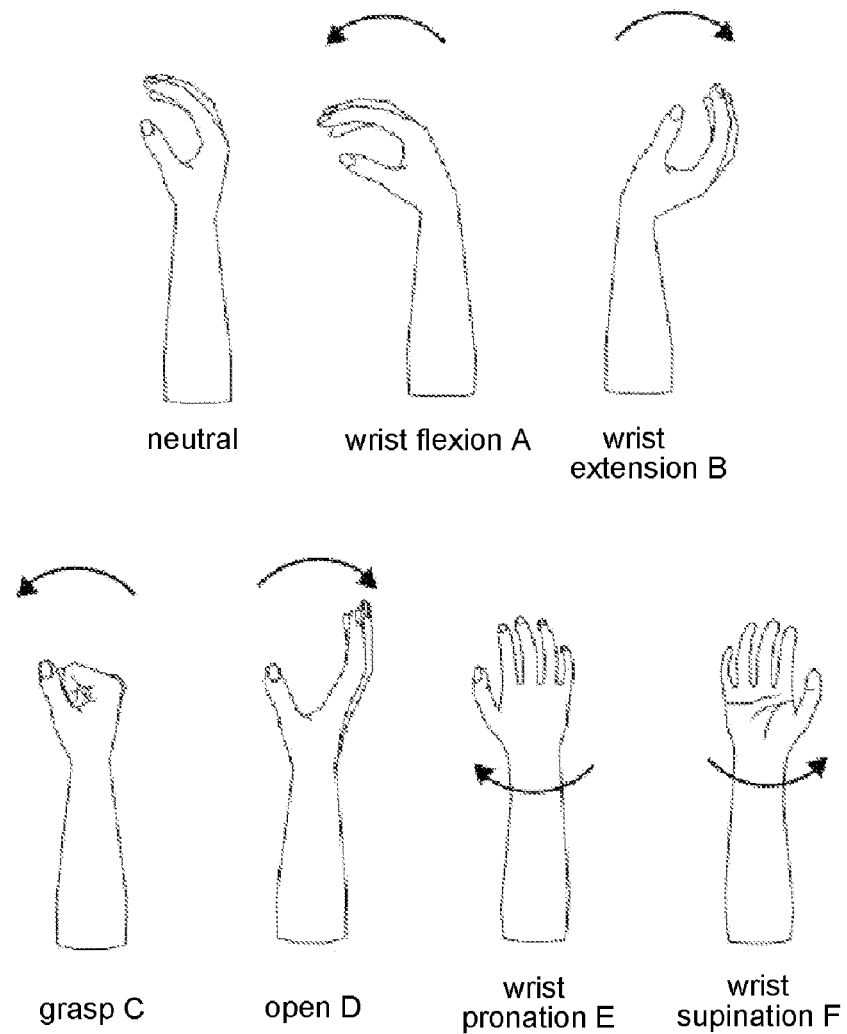
FIG. 2 illustrates the motion classification system in embodiment 1 of the present invention classifying six types of wrist motions of a subject.

FIG. 2 illustrates the motion classification system in embodiment 1 of the present invention classifying six types of wrist motions of a subject.

As described in FIG. 1, the motion classification system S (motion operational estimating system, event type estimating system, classification estimating system) comprises: a surface EMG measuring apparatus U1 (measuring device, surface EMG signal measuring device) to measure surface EMG signal (biosignal) based on muscle motion (action of muscle group) accompanying to the operational decision (event) of a subject as a member of human being; a Client PC (operating terminal such as computer, personal computer which can be operated by a user) used as the main unit for motion classification in order to classify motions of said subject which is connected to said surface EMG measuring apparatus U1.

Additionally, as described in FIG. 2, seven types of motions, namely ┌wrist flexion┘ (┌motion A┘), ┌wrist extension┘ (┌motion B┘), ┌hand grasp┘ (┌motion C┘, ┌hand extension┘ (┌motion D┘, wrist supination(┌motion E□), ┌wrist pronation┘ (┌motion F┘), including ┌neutral┘ (┌motionless┘, no motion being classified), are classified in embodiment 1.

As described in embodiment 1, said surface EMG measuring apparatus U1 comprises six EMG sensors (the six measuring devices including the first measuring device, the second measuring device, . . . , the six measuring device) SN1~SN6 to measure six measuring sections (the first measuring section, the second measuring section, . . . , the six measuring section) pre-set on the fore wrist of said subject. In detail, the six measuring sections are arranged on skin of right wrist adjacent to elbow of said subject, regarding to the six types of muscles such as flexor carpi radialis muscle, flexor digitorum profundus muscle, flexor carpi ulnaris muscle, extensor digitorum muscle, flexor carpi radialis longus muscle, and brachioradialis muscle. Additionally, the six pairs of wet electrodes (6 ch) attached to the six sections on skin of said subject indicates said six EMG sensors SN1~SN6. Moreover, compared with dry electrode where said paste is not coated, said wet electrode, having a conductive paste coated on the electrode, can ensure a stable measurement which will not be interfered by the skin's condition.

That is to say, with said surface EMG measuring apparatus U1, the surface EMG signals (six types of biosignals, the first information, the second information, . . . , the sixth information) are measured regarding to said six types of muscles as described in embodiment 1 by way of the six pairs of wet electrodes (SN1~SN6) attached to the skin of said six positions.

In addition, said Client PC used for motion classification as described in embodiment 1 is a computer unit which comprises a computer H1, display H2, input devices such as keyboard H3 and mouse H4 el, and a HD driver (hard disk driver) which is not shown in the figures.

The motion classification apparatus (operational decision estimating apparatus, event type estimating apparatus, classification estimating apparatus) (U1+PC) described in embodiment 1 comprises said surface EMG measuring apparatus U1 and said classifying Client PC.

(Description of Control Unit in Embodiment 1)

Figure 3:
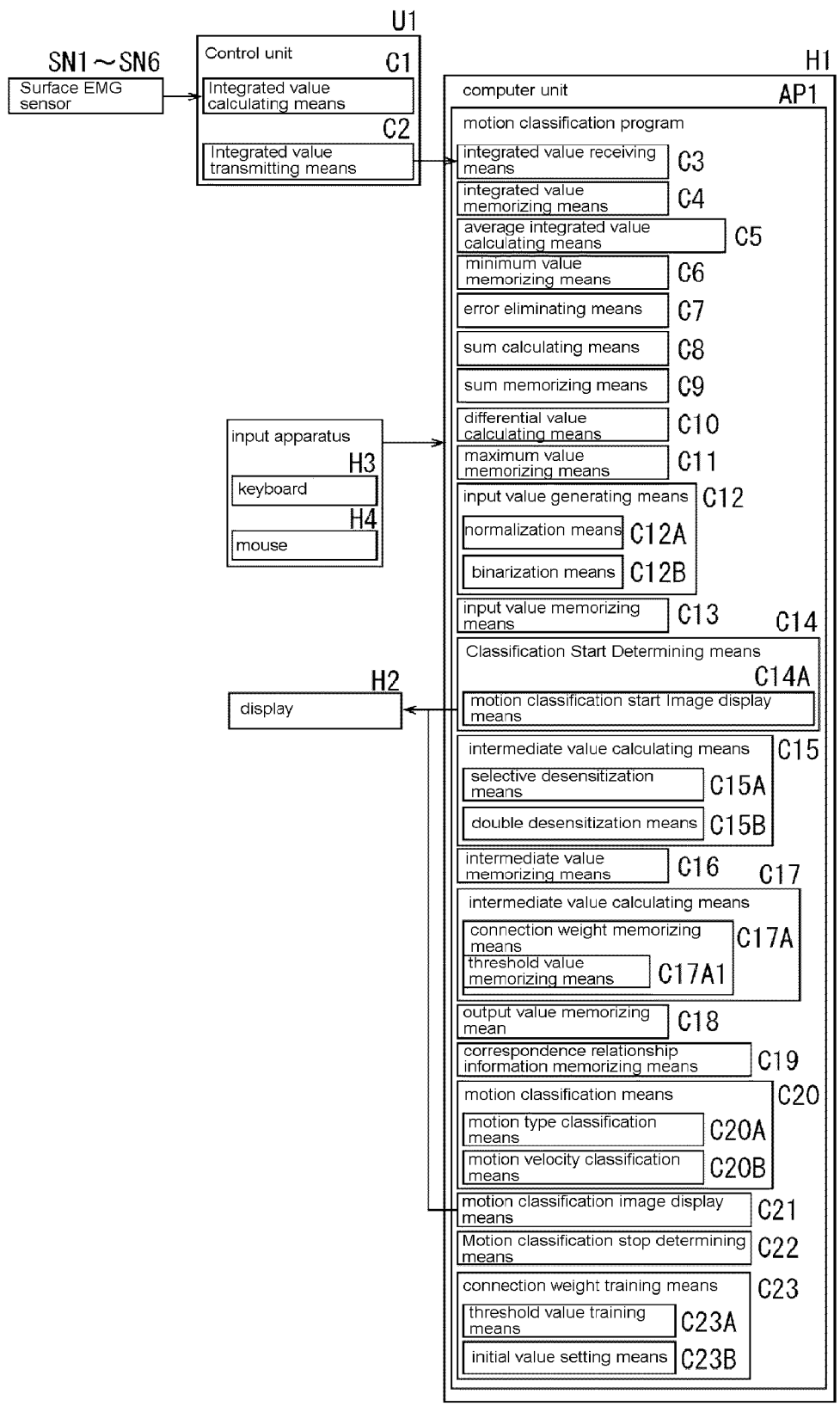
FIG. 3 is a block diagram depicting the function of each components of the motion classification system (function block diagram) in embodiment 1 of the present invention.

FIG. 3 is a block diagram depicting the function of each components of the motion classification system (function block diagram) in embodiment 1 of the present invention.

As described in FIG. 3, the control unit of said surface EMG measuring apparatus U1 and the computer H1 of said classifying Client PC comprises a I/O device (interface of input or output) to perform input or output operation of signals between the system and the outside world, and to adjust the level of input or output signals; a ROM (read only memory, recording media) to memorize programs and data necessary for booting process; a RAM (random access memory, recording media) to memorize temporarily the necessary data and programs; a CPU (central processing unit) to perform operation regarding to the booting programs memorize in said ROM el; a blocking oscillator, thus the various function are realized by performing the programs memorized in ROM and RAM el. the motion classification program AP1 (operational decision estimating program, event type estimating program, classification estimating program) is memorized in the ROM of said control unit as described in embodiment 1.

(signal input component connected to the control unit of the surface EMG measuring apparatus U1)

The following output signals from the signal output component (SN1~SN6) are input into the control unit of said surface EMG measuring apparatus U1.

SN1~SN6: EMG sensors

The surface EMG signals of said six types of muscles measured at six measuring positions are input into said control unit by six EMG sensors SN1~SN6.

(function of the control unit of the surface EMG measuring apparatus U1)

Said surface EMG measuring apparatus U1 comprises the following function realizing means in order to calculate the output signals input into said classifying Client PC according to the output signals from said six EMG sensors of SN1~SN6.

C1: An Integrated Value Calculating Means

An integrated value calculating means C1 is a means to calculate the integrated values (the first integrated value $s_1$, the second integrated value $s_2$, ..., the sixth integrated value $s_6$) of six surface EMG signals measured by said six EMG sensors SN1~SN6 to obtain the integrated surface EMG signals (integrated EMG, IEMG: Integrated Electro Myo-Gram) ($s_1$~$s_6$).

By using said integrated value calculating means described in embodiment 1, calculation is made for the six integrated surface EMG signals ($s_1$~$s_6$) through smoothing with full wave rectification respectively for said six surface EMG signals obtained at a sampling frequency of 3 [kHz]. Specifically, regarding the six surface EMG signals, full wave rectification is performed to convert alternating current having a whole waveform of positive as well as negative current to direct current, wherein negative current is transferred into positive current which is symmetric to the negative current; subsequently, smoothing, namely low-pass filtering is performed with a given cut-off frequency to calculate the six integrated surface EMG signals ($s_1$~$s_6$). In addition, said cut-off frequency is set as 2.4[Hz] in embodiment 1.

C2: An Integrated Value Transmitting Means

An integrated value transmitting means C2 is a means to transmit said six integrated surface EMG signals ($s_1$~$s_6$) calculated by said integrated value calculating means C1 to the computer unit H1 of said classification Client PC. As described in embodiment 1, in respect to said six integrated surface EMG signals (s1~s6), the values of the integrated surface EMG signals ($s_1$~$s_6$) which are measured three times (($3 \times 10^3) \times 10^{-3} = 3$)) at an interval of 1 [ms] are transmitted respectively to the computer unit H1 of said classification Client PC by means of said integrated value transmitting means based on a sampling frequency of 3 [Hz].

(Function of the Control Unit of the Computer Unit H1 of the Classification Client PC)

Additionally, in respect to the said motion classifying program AP1 to classify motions of said subject, the control unit of said surface EMG measuring apparatus U1 comprises the following function realizing means based on the output signals, namely the integrated surface EMG signals ($s_1$~$s_6$), of said surface EMG measuring apparatus U1.

C3: An Integrated Value Receiving Means

An integrated value receiving means C3 is a means to receive said six integrated surface EMG signals ($s_1$~$s_6$) transmitted by said integrated value transmitting means C2. As described in embodiment 1, in respect to said six integrated surface EMG signals ($s_1$~$s_6$), the values of said integrated surface EMG signals ($s_1$~$s_6$) are received three times respectively within an interval of 1 [ms] by means of said integrated value receiving means C3.

C4: An Integrated Value Memorizing Means

An integrated value memorizing means C4 is a means to memorize said six integrated surface EMG signals ($s_1$~$s_6$) received by said integrated value receiving means C3. As described in embodiment 1, in respect to said six integrated surface EMG signals ($s_1$~$s_6$), the values of said integrated surface EMG signals ($s_1$~$s_6$) which are received three times within each 1 [ms] are memorized respectively by means of said integrated value memorizing means C4.

C5: An Average Integrated Value Calculating Means

An average integrated value calculating means C5 is a means to calculate the average integrated values (the first average integrated value $v_1$, the second average integrated value $v_2$, ..., the sixth average integrated value $v_6$, AIEMG: Average Integrated Electro Myo-Gram) according to a certain pre-set time frame which are the average values of said six integrated surface EMG signals ($s_1$~$s_6$) within a given time frame.

Figure 4:
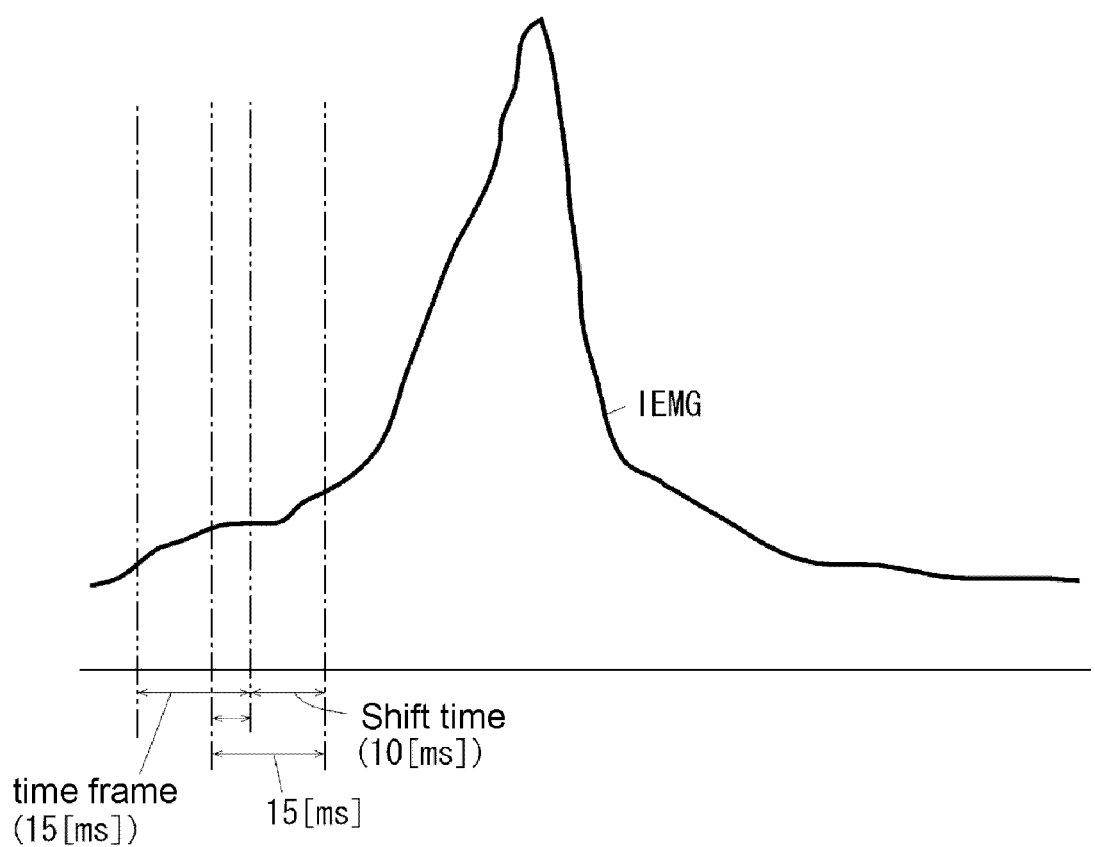
FIG. 4 illustrates the average integrated values in embodiment 1 of the present invention.

FIG. 4 illustrates the average integrated value in embodiment 1 of the present invention.

As described in FIG. 4, said six average integrated values ($v_1$~$v_6$) are obtained by calculating respectively the average ($v_1$~$v_6$) of said six surface EMG signals ($s_1$~$s_6$) that are received three times for each interval of 1 [ms], wherein said time frame is 15 [ms], said shift time is 10 [ms] by way of the average integrated value calculating means C5. In other words, by way of said average integrated value calculating means C5, the average values ($v_1$~$v_6$) of 45 signals ($3 \times 15 = 45$) of the integrated surface EMG signals ($s_1$~$s_6$) within one frame of 15 [ms] while shifting every 30 signals ($3 \times 10 = 30$) are calculated respectively and then noise interference is removed.

When the first average integrated value v1 is calculated over frame time while the first integrated value $s_1$ at point Q is received and shifted every P points within one frame time, each value of the first integrated value $s_1$ is defined as I EMG$_1$ (q) (q=1, 2, ... ), and the first average integrated value $v_1$ at the p-th frame time is defined as A I EMG$_1$ (p) (p=1, 2, ... ), then the first average integrated value $v_1$ within the p-th frame time A I EMG$_1$ (p) is defined in the following equation (2-1).

Besides, in embodiment 1, Q is determined to be 45 and P to be 30.

$$AIEMG_1(p) = \{IEMG_1(1+P\times(p-1)) + IEMG_1(2+P\times(p-1)) + \ldots + IEMG_1(Q+P\times(p-1))\}/Q \qquad \text{equation (2-1)}$$

Likewise, each value ($A\,I\,EMG_2$ (p)~$A\,I\,EMG_6$ (p)) of the other average integrated value ($v_2$~$v_6$), can be expressed by said equation (2-1). Consequently, if the number of each channel is represented by I (i=1, 2, . . . ), average integrated value (A I EMG, (p) of each average integrated value $v_i$ at p-th frame time can be expressed as given in the following equation (2-2).

$$AIEMG_i(p) = \{IEMG_i(1+P\times(p-1)) + IEMG_i(2+P\times(p-1)) + \ldots + IEMG_i(Q+P\times(p-1))\}/Q \qquad \text{equation (2-2)}$$

C6: Minimum Value Memorizing Means

With respect to said six average integrated values ($v_1$~$v_6$), the minimum values of said six average integrated values ($v_1$~$v_6$) calculated by way of said average integrated value calculating means C5 are memorized respectively by way of the Minimum Value Memorizing Means C6. Moreover, as described in embodiment 1, if, among the A I $EMG_i$ (p) value of said six average integrated value $v_i$ over frame time, the minimum six values from the first to the p-th frame time are respectively represented by $\epsilon_i$, said minimum value $\epsilon_i$ can be expressed as given in the following equation (3).

$$\epsilon_i = \min[AIEMG_i(p)] \qquad \text{equation (3)}$$

C7: Error Eliminating Means

Error Eliminating Means C7 is a means to eliminate error from said six average integrated values ($v_1$~$v_6$) calculated by the average integrated value calculating means C5. As described in embodiment 1, said six minimum values E, which are memorized by said Minimum Value Memorizing Means, are considered as error of said individual subject, namely noise (i.e. individual difference). By way of the error eliminating means C7, the error is eliminated from the A I EMG, (p) value of said six average integrated value $v_i$ over frame time. Specifically, if the true value of said six average integrated value $v_i$ after error being eliminated is represented by A I $EMG\epsilon_i(p)$, said error eliminated value A I EMGE, (p) can be expressed as given in the following equation (4).

$$AIEMG\epsilon_i(p) = AIEMG_i(p) - \epsilon_i \qquad \text{equation (4)}$$

C8: Sum Calculating Means

Sum Calculating Means C8 is a means to calculate the sum of said six average integrated values ($v_1$~$v_6$) after error being eliminated by the error eliminating means C7. as described in embodiment 1, the sum of the true value the A I $EMG\epsilon_i$ (p) of said six average integrated value $v_i$ over frame time after error being eliminated are calculated by the Sum Calculating Means C8. Specifically, if the sum of said six average integrated value $v_i$ over frame time is A I $EMG_{all}$ (p), said A I $EMG_{all}$ (p) can be expressed as given in the following equation (5).

$$AIEMG_{all}(p) = AIEMG_{\epsilon_1}(p) + AIEMG_{\epsilon_2}(p) + \ldots + AIEMG_{\epsilon_6}(p) \qquad \text{equation (5)}$$

C9: Sum Memorizing Means

Sum Memorizing Means C9 is a means to memorize the A I $EMG_{all}$ (p) (p-1) which is the sum of said six average integrated values ($v_1$~$v_6$) at a previous frame time calculated by said Sum Calculating Means C8.

C10: Differential Value Calculating Means

Differential Value Calculating Means C10 is a means to calculate the differential value of the sum A I $EMG_{all}$ (p) of said six average integrated value $v_i$ over frame time calculated by said Sum Calculating Means C8. As described in embodiment 1, the differential values between the sum A I $EMG_{all}$ (p) (the first sum) calculated by said Sum Calculating Means C8, and the sum A I $EMG_{all}$ (p-1) (the second sum) at previous frame time memorize by said sum memorizing means C9, are calculated by said Differential Value Calculating Means C10. Specifically, if said differential value is represented by A I $EMG_{dif}$ (p), said differential value A I $EMG_{mf}$ (p) can be expressed as given in the following equation (6).

$$AIEMG_{dif}(p) = AIEMG_{all}(p) - AIEMG_{all}(p-1) \qquad \text{equation (6)}$$

C11: Maximum Value Memorizing Means

The maximum value of said six average integrated value $v_i$ from the first to the p-th frame time for each A I EMGE, (p); the maximum value from the first to the p-th frame time for each of said A I $EMG_{all}$ (p); and the maximum value from the first to the p-th frame time for each of said A I $EMG_{dif}$(p); are memorized by the Maximum Value Memorizing Means C11. As described in embodiment 1, if the maximum value of said A I $EMG\epsilon_i$ (p) is represented by A I $EMG\epsilon_{imax}$, the maximum value of said A I $EMG_{all}$ (p) is represented by A I $EMG_{amax}$, and the maximum value of said A I $EMG_{dif}$(p) is represented by A I $EMG_{dmax}$, the eight maximum values A I $EMG\epsilon_{imax}$, A I $EMG_{amax}$, A I $EMG_{dmax}$ expressed as given in the following equations (7-1)~(7-3) are memorized by the Maximum Value Memorizing Means C11.

$$AIEMG\epsilon_{imax} = \max[AIEMG\epsilon_i(p)] \qquad \text{equation (7-1)}$$

$$AIEMG_{amax} = \max[AIEMG_{all}(p)] \qquad \text{equation (7-2)}$$

$$AIEMG_{dmax} = \max[AIEMG_{dif}(p)] \qquad \text{equation (7-3)}$$

C12: Input Value Generating Means

Input Value Generating Means C12 is a means comprising Normalization means C12A and Binarization Means C12B, to generate input values (values of input variables) which are input into a below-mentioned selective desensitization neutral network (SDNN).

C12A: Normalization Means

Normalization Means C12A is a means to generate 8 kinds of input values at every frame time according to normalization, which is performed by dividing said A I $EMG\epsilon_i$ (p) of the six average integrated value $v_i$, said sum A I $EMG_{all}$ (p), and said differential value A I $EMG_{dif}$ (p) to their maximum values A I $EMG\epsilon_{imax}$, A I $EMG_{amax}$, and A I $EMG_{dmax}$ respectively. More specifically, if eight kinds of normalization values (input value) are $N_i(p)$ (i=1, 2, . . . , 6), $N_a(p)$, $N_d(p)$, said eight kinds of normalization values $N_i(p)$, $N_a(p)$, $N_d(p)$ are expressed as given in the following equations (8-1)~(8-3).

$$N_i(p) = AIEMG\epsilon_i(p)/AIEMG\epsilon_{imax} \qquad \text{equation (8-1)}$$

$$N_a(p) = \ln(AIEMG_{all}(p)+1)/\ln(AIEMG_{amax}+1) \qquad \text{equation (8-2)}$$

$$N_d(p) = AIEMG_{dif}(p)/AIEMG_{dmax} \qquad \text{equation (8-3)}$$

Additionally, in respect to the normalized sum $N_a(p)$, there exists a possibility that the difference between said sum A I $EMG_{all}(p)$ and said A I $EMG_{amax}$ is too significant, as shown in said equation (8-2). Thus as described in embodiment 1, normalization is performed in the range of 0~1, on the value obtained from dividing the normalized sum Na(p) by ln(A I EMGall (p)+1) and ln(A I EMGamax+1), where the value of natural logarithm is over o. In addition, as shown in said equation (8-3), for the normalized value Nd(p), when A I EMGdif (p)<0 and Nd(p)<0, it is regarded as Nd(p)=0.

C12B: Binarization Means

Binarization Means C12B is a means to convert said eight kinds of input values Ni(p), Na(p), Nd(p) calculated by said normalization means into a binarized expression. As described in embodiment 1, said eight kinds of input values Ni(p), Na(p), Nd(p) are converted respectively into values that can be represented by fifteen +1 and fifteen −1, namely, binary vectors with fifteen +1 and fifteen −1 as vector components the way of said Binarization Means C12B. More specifically, the normalized input values Ni(p), Na(p), Nd(p) might be in the range of 0~1($0 \leq N_i(p) \leq 1$, $0 \leq N_a(p) \leq 1$, $0 \leq N_d(p) \leq 1$). Therefore, when the normalize value is 0, binarization is performed for the fifteen vector components from the first to the fifteenth to become +1, while the fifteen vector components from the sixth to the thirtieth to become +1. That is to say, binary conversion is made as expressed in the following equation (9-1).

$$0 = (+1, +1, \ldots +1, -1, -1, \ldots, -1) \quad \text{equation (9-1)}$$

Next, when only the value 1/15(0.0666 . . . ) turns out to be big, shift the continuous fifteen +1 to the right each at one time. For example, in the case of 0.1(1/15<0.1<2/15), shift to the right as shown in the following equation (9-2).

$$0.1 = (-1, +1, +1, \ldots +1, -1, -1, \ldots, -1) \quad \text{equation (9-2)}$$

Subsequently, in the case of 1(15/15=1), the conversion is performed for the fifteen vector components from the first to the fifteenth to become +1, while the fifteen vector components from the sixth to the thirtieth to become +1. In other words, conversion is performed as shown in the following equation (9-3).

$$1 = (-1, -1, \ldots, -1, +1, +1, \ldots +1) \quad \text{equation (9-3)}$$

Figure 5:
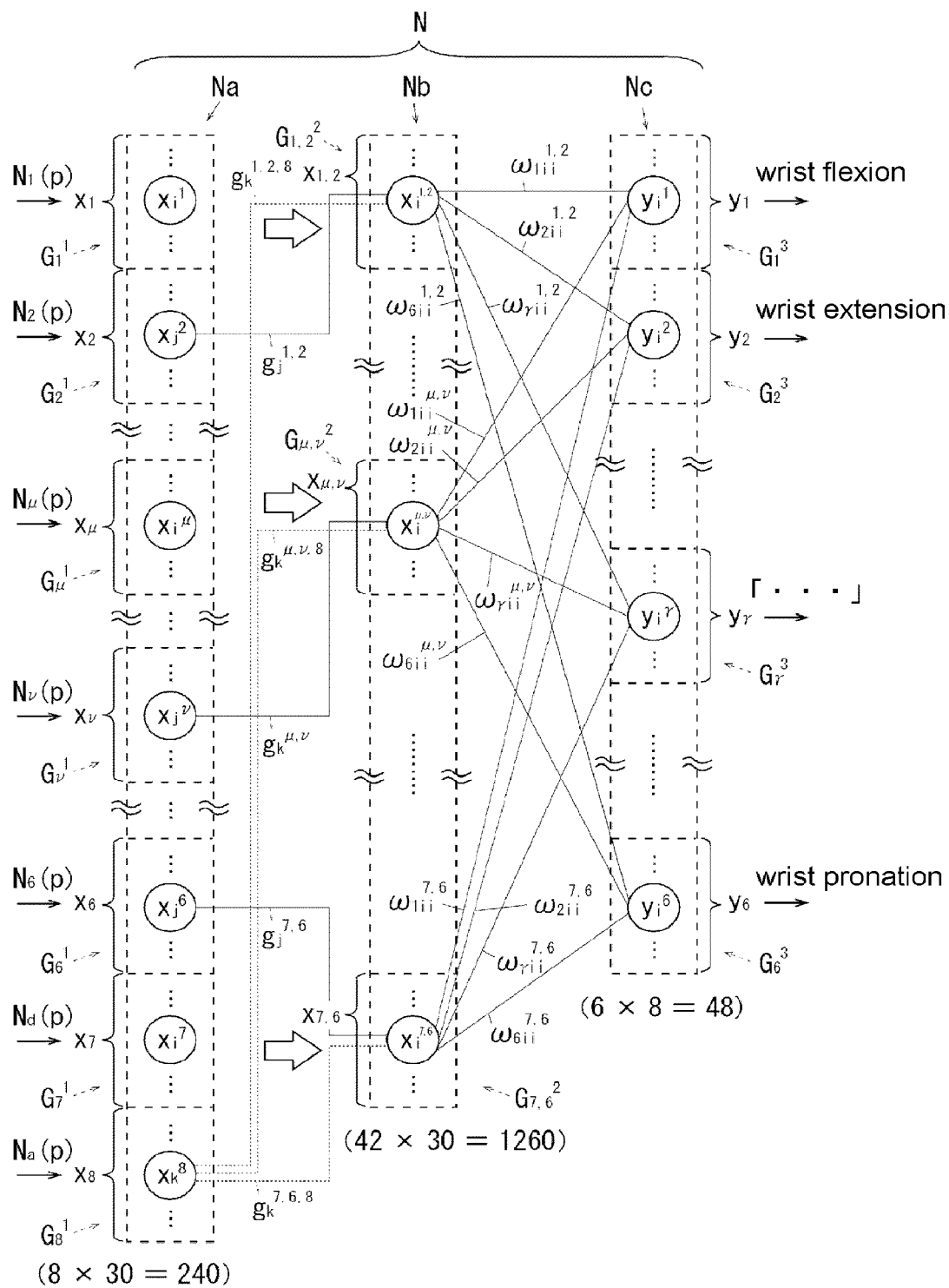
FIG. 5 illustrates a selective desensitization neutral network in embodiment 1 of the present invention.

FIG. 5 illustrates a selective desensitization neutral network in embodiment 1 of the present invention.

C13: Input Value Memorizing Means

Input Value Memorizing(Input) Means C13 is a means to memorize said eight kinds of input values $N_i(p)$, $N_a(p)$, $N_d(p)$ generated by said Input Value Generating Means C12. As described in embodiment 1, said eight input values $N_i(p)$, $N_a(p)$, $N_d(p)$ that are converted by way of said Binarization Means C12B into values that can be represented by vector components of fifteen +1 and fifteen −1 are memorized by the Input Value Memorizing Means C13.

Here, as described in embodiment 1, motions of said subject is classified by inputting said eight input values Ni(p), Na(p), Nd(p) that vary according to shift time into the selective desensitization neutral network shown in FIG. 5. As shown in FIG. 5, said selective desensitization neutral network in embodiment 1 comprises an input layer Na (input element group) consisting of 240 elements (input elements)

Said input layer Na in embodiment 1 comprises eight input element groups (first input element group $G_1^1$, second input element group $G_2^1$, . . . difference input element group $G_7^1$ as the seventh input element group and sum input element group (multiplex element group) $G_8^1$ as the eighth input element group), wherein said eight input element group $G_i^1$ (i=1, 2, . . . , 8) each comprises 30 elements respectively(8× 30=240).

Additionally, regarding said input layer Na in embodiment 1, said eight input element groups $G_i^1$ are pre-set according to the values of said eight input variables (first input variable $x_1$, second input variable $x_2$, . . . , the seventh input variable $x_7$, the eighth input variable $x_8$) namely said eight input values $N_i(p)$, $N_a(p)$, $N_d(p)$.

Subsequently, if each value of the elements of input element group Gi1 is represented by $x_1^i, x_2^i, \ldots, x_{30}^i$, each input variable can be expressed as given in the following equations (10).

$$X_i = (x_1^i, x_2^i, \ldots, x_{30}^i) \quad \text{equations (10)}$$

Besides, let x denote the component of the 8-dimensional vector for said eight input values $N_i(p)$, $N_a(p)$, $N_d(p)$, then said input vectors can be expressed as given in the following equations (11).

$$x = (x_1, \ldots, x_7, x_8) = (N_1(p), \ldots, N_d(p), N_a(p)) \quad \text{equation (11)}$$

Furthermore, regarding the 30 elements of each said input element group Gi1, either the value of +1 or −1 ($x_1^i \sim x_{30}^i$) can be input (maintained). Thus, by memorizing (updating) the vector expression at each shift time which are obtained through binarization of each input values $N_i(p)$, $N_a(p)$, $N_d(p)$, the values of thirty elements ($x_1^i \sim x_{30}^i$) of each said input element group $G_i^1$ are regarded as being input at every shift time. As described in embodiment 1, let $N_i(p)$ be input value, the values (+1,−1) of eight input element group namely totally 240 values (30×8=240) comprising values of 30 elements (+1,+1, . . . ,+1,−1,−1, . . . ,−1) are memorized.

Figure 6:
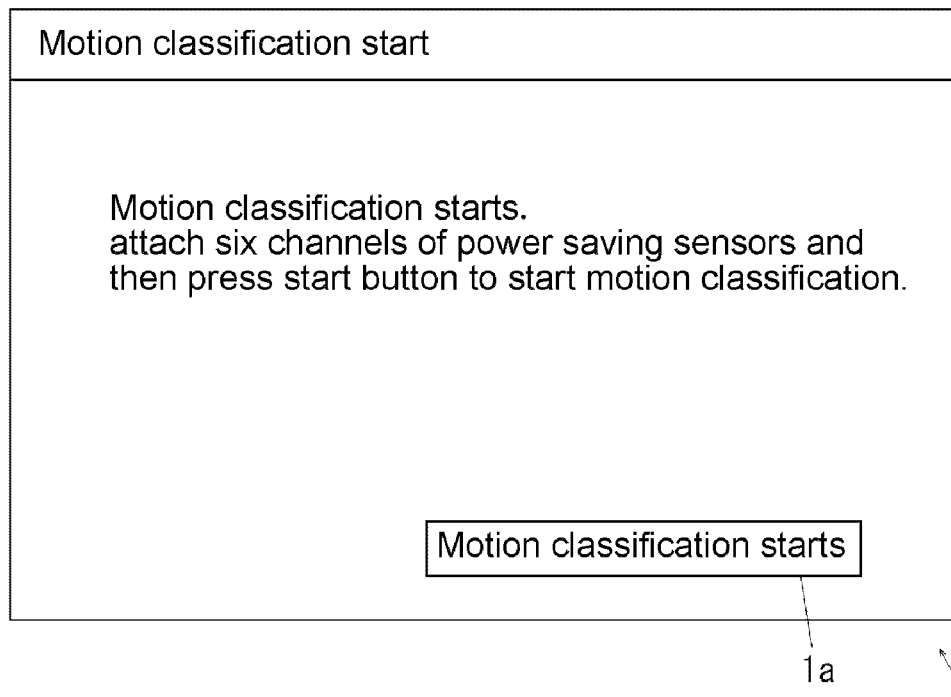
FIG. 6 illustrates the at motion classification start image in embodiment 1 of the present invention.

FIG. 6 illustrates the display at motion classification start Image in embodiment 1 of the present invention.

C14: Motion Classification Start Determining Means

Motion Classification Start Determining Means C14, comprising motion classification start Image display means C14A to display the motion classification start Image as shown in FIG. 6, is a means to decide whether or not to start motion classification of said subject. More specifically, as described in FIG. 6 of embodiment 1, by way of said Motion Classification Start Determining Means C14, it is decided whether or not to start motion classification by whether or not to select the classification start button 1a on said motion classification start image.

C15: Intermediate value calculating means

Intermediate value calculating means C15, comprising selective desensitization means C15A and double desensitization means, is a means to calculate, when it has been decided to start motion classification by said subject by way of said Motion Classification Start Determining Means C14, the intermediate values (value of intermediate variable) over shift time based on said eight input values $N_i(p)$, $N_a(p)$, $N_d(p)$ which are memorized into said input layer Na.

As described in FIG. 5, said selective desensitization neutral network N comprises an intermediate layer (intermediate element group) consisting of 1260 elements (intermediate element) connected with 240 elements of said input layer Nb.

Said intermediate layer Nb in embodiment 1 comprises 42 intermediate element group (the first intermediate element group $G_{1,2}^2$, the second intermediate element group $G_{2,1}^2$, . . . , the 42nd intermediate element group $G_{7,6}^2$), and said 42 intermediate element group $G_{\mu,v}^2$ ($\mu \neq v$, $\mu=1, 2, \ldots, 7$, $v=1, 2, \ldots, 7$) comprise 30 elements respectively (42× 30=1260).

On said intermediate layer Nb in embodiment 1, the total 42 intermediate element group $G_{\mu,v}^2$ based on said modified group $G_\mu^1$ are pre-set, which are obtained from modifying said modification group $G_v^1$ through product type modification, wherein except the normalized sum $N_a(p)$, one of the seven input element group ($G_1^1 \sim G_7^1$) corresponding to seven input values $N_i(p)$, $N_a(p)$ is given as the modified group $G_\mu^1$ ($\mu=1, 2, \ldots, 7$), and one of the six input element group ($G_1^1 \sim G_7^1$) except $G_\mu^1$ is given as the $G_v^1$ ($v \neq \mu$, $v=1, 2, \ldots, 7$).

Here, if each value of thirty element of the intermediate element group $G_{\mu,v}^2$ ($\mu \neq v$, $\mu=1, 2, \ldots, 7$, $v=1, 2, \ldots, 7$) is represented by $x_1^{\mu,v}, x_2^{\mu,v}, \ldots, x_{30}^{\mu,v}$, each intermediate variable $x_{\mu,v}$ can be expressed as given in the following equation (12).

$$x_{\mu,v} = (x_1^{\mu,v}, x_2^{\mu,v}, \ldots, x_{30}^{\mu,v}) \qquad \text{equation (12)}$$

Furthermore, product type modification is a method to change values $x_1^\mu \sim x_{30}^\mu$ of the element of said modified group $G_\mu$ according to the values $x_1^v \sim x_{30}^v$ of the element of said modification group $G_v$. More specifically, as depicted by the solid line in FIG. 5, if the pre-calculated value of the output sensitivity (gain) according to the values $x_1^v \sim x_{30}^v$ of the element of said modification group $G_v$ is represented by $g_1^{\mu,v} \sim g_{30}^{\mu,v}$, the product type modification refers to calculation of product $\{(x_i^\mu) \times (g_j^{\mu,v})\}$ between of value $x_i^\mu$ (i=1, 2, ..., 30) of said modified group $G_\mu$ and value of said output sensitivity $g_j^{\mu,v}$ (j=1, 2, ..., 30)

In this case, especially when said output sensitivity $g_j^{\mu,v}$ is 0 causing said $\{(g_j^{\mu,v}) \times (x_i^\mu)\}$ to be 0, in other words, when $g_j^{\mu,v}=0$ resulting $\{(g_j^{\mu,v}) \times (x_i^\mu)\}=0$, it is called desensitization. Additionally, selective desensitization means randomly desensitizing the value of a part of elements $x_i^\mu$ (i=1, 2, ..., 30) of said modified group $G_\mu$.

Besides, product type modification of modified group $G_\mu^1$ according to modification group $G_v^1$ is referred to as $G_\mu^1$ ($G_v^1$) in the below description.

What is more, as described in embodiment 1, product type modification is furthermore performed on said product type modification $G_\mu^1$ ($G_v^1$) according to the sum input element group $G_8^1$ corresponding to the normalized sum $N_a(p)$. More specifically, in the case that values of the sum output sensitivity (values of multiplex output sensitivity) pre-calculated by values $x_1^8 \sim x_{30}^8$ of the element of said sum input element group $G_8^1$ are referred to as $g_1^{\mu,v,8} \sim g_{30}^{\mu,v,8}$, as shown by the dot line in FIG. 5, the product between said product $\{(g_j^{\mu,v}) \times (x_i^\mu)\}$ and the value of said sum output sensitivity $g_k^{\mu,v,8}$ (k=1, 2, ..., 30) is defined as the values $x_i^{\mu,v}$ (i=1, 2, ..., 30) of element of said intermediate element group $G_{\mu,v}^2$. Thus, the values $x_i^{\mu,v}$ of the element of said intermediate element group $G_{\mu,v}^2$ can be expressed as given in the following equations (13).

$$x_i^{\mu,v} = (g_k^{\mu,v,8}) \times (g_j^{\mu,v}) \times (x^\mu) \qquad \text{equation (13)}$$

Additionally, each value of said output sensitivity $g_j^{\mu,v}$, $g_k^{\mu,v,8}$ in embodiment 1 can be expressed as given in the following equations (14-1)□(14-2)□(14-1)'□(14-2)'.

$$g_j^{\mu,v} = (1+x_j^v)/2 \qquad \text{equation(14-1)}$$

$$j = \sigma(i) \qquad \text{equation (14-2)}$$

$$g_k^{\mu,v,8} = (1+x_k^8)/2 \qquad \text{equation (14-1)'}$$

$$k = \sigma'(i) \qquad \text{equation (14-2)'}$$

That is to say, when each value $x_j^v$, $x_k^8$ of the input element group $G_8^1$, $G_v^1$ is +1, each value $g_j^{\mu,v}$, $g_k^{\mu,v,8}$ is +1 as well; when each value $x_j^v$, $x_k^8$ of the input element group $G_8^1$, $G_v^1$ is −1, each value $g_j^{\mu,v}$, $g_k^{\mu,v,8}$ becomes 0 as being desensitized.

Here, $\sigma(i)$ and $\sigma'(i)$, as random functions, refer to the value (a random value from 1 to 30) of the ith element of permutations such as (21,15, ... 4) or (17,6, ..., 8), which are replaced randomly from the permutation (1,2, ..., 30).

In addition, if said random functions $\sigma(i)$ and $\sigma'(i)$ are not applied, when there exhibits strong correspondence between said modified group $G_\mu^1$ and said modification group $G_v$ as well as the sum input element group $G_\mu^1$, there exists high possibility that either almost all the elements of said modified group $G_\mu^1$ are selectively desensitized, or almost all the elements of said modified group $G_\mu^1$ are not selectively desensitized, or only the elements in which $x_i^\mu=1$ are selectively desensitized, or only the element in which $x_i^\mu=-1$ are selectively desensitized, thus causes significant decrease in performance of motion classification. As a result, said random functions $\sigma(i)$ and $\sigma'(i)$ are used to weaken the correspondence between said element groups $G_\mu^1$, $G_v$ and $G_8^1$.

Here, equation (13) can be given in the following form by substituting said equations (14-1), (14-2), (14-1)', (14-2)' into said equation (13).

$$x_i^{\mu,v} = \{(1 + x_{\sigma'(i)}^8)/2\} \times \{(1 + x_{\sigma(i)}^v)/2\} \times x_i^\mu \qquad \text{equation (13)'}$$

That is to say, as described in embodiment 1, the value $x_i^{\mu,v}$ of the element of said intermediate element group $G_{\mu,v}^2$ refer to the values that, after selective desensitization based on the value $x_i^\mu$ of said modified group $G_\mu^1$ and the value s of said output sensitivity $g_j^{\mu,v}$, are furthermore selectively desensitized (double desensitization, multiple desensitization) according to the values of said sum output sensitivity; namely, the values $x_i^\mu$ of a pertinent number of 15~30 in said modified group $G_\mu^1$ that are selectively desensitized.

As described in embodiment 1, 42 gain vectors (the first gain vector $G_{1,2}^1$, the second gain vector $G_{2,1}^1$, ..., the 42nd gain vector $G_{7,8}^1$) comprise accumulation of 42 output sensitivity values (the first output sensitivity value $g_j^{1,2}$, the second sensitivity value $g_j^{1,2}$, ..., the 42nd sensitivity value $g_j^{7,6}$), while 42 sum gain vectors (the first sum gain vector $G_{1,2,8}^1$, the second sum gain vector $G_{2,1,8}^1$, ..., the 42nd sum gain vector $G_{7,6,8}^1$) comprise accumulation of 42 sum output sensitivity values (the first sum output sensitivity value (the first multiplex sensitivity) $g_k^{1,2,8}$, the second sensitivity value (the second multiplex sensitivity) $g_k^{2,1,8}$, ..., the 42nd sensitivity value (the 42nd multiplex sensitivity) $g_k^{7,6,8}$).

Consequently, after calculation of said 42 gain vector $G_{\mu,v}1$ and said 42 sum gain vector $G_{\mu,v,8}^1$ corresponding to the 42 intermediate element group $G_{\mu,v}^2$ by way of said intermediate value calculating means C15 described in embodiment 1, the values of 42 intermediate variables (intermediate value) $x_{\mu,v2}$ ($\mu \neq v$, $\mu=1, 2, \ldots, 7$, $v=1, 2, \ldots, 7$) are calculated through double desensitization of the values $x_i^{\mu,v}$ of the element of 42 intermediate element group $G_{\mu,v}^2$.

Accordingly, the values of said 42 intermediate variables $x_{\mu,v}$ in embodiment 1, namely said intermediate values can be expressed as a thirty-dimensional vector (three valued pattern), for instance, (+1,0,0,−1,+1,...,0) with the three values of −1, 0, +1 as vector components.

C15A: Selective Desensitization Means

Selective desensitization means C15A comprises output sensitivity calculating means C15A1 which calculates the values of said 42 output sensitivity $g_j^{\mu,v}$ according to said equations (14-1) and (14-2), as shown by the solid line in FIG. 5, the values $x_i^\mu$ of a pertinent number in said modified group $G_\mu^1$ are selectively desensitized by the values $g_j^{\mu,\nu}$ of said 42 output sensitivity.

C15B: Double Desensitization Means

Double desensitization means (multiple desensitization means) C15B comprises output sensitivity calculating means C15B1 which calculates the values of said 42 output sensitivity $g_k^{\mu,\nu,8}$ according to said equations (14-1)' and (14-2)', as shown by the dot line in FIG. 5 and said equations (13) and (13)', the values $x_i^\mu$ of a pertinent number in said modified group $G_\mu^1$ are doubly desensitized by selectively desensitizing the values of elements of a pertinent number in said productive modification group $G_\mu^1$ ($G_\nu^1$), namely said product $\{(g_j^{\mu,\nu}) \times (x_i^\mu)\}$ according to the values $g_k^{\mu,\nu,8}$ of said 42 sum output sensitivity.

C16: Intermediate Value Memorizing Means

Intermediate value memorizing means (Intermediate value input means) C16 is a means to memorize said 42 intermediate values calculated by said Intermediate value calculating means C15, namely values of said 42 intermediate variables $x_{\mu,\nu}$ ($\mu \neq \nu$, $\mu=1, 2, \ldots, 7$, $\nu=1, 2, \ldots, 7$). By way of the intermediate value memorizing means C16, the values $x_j^{\mu,\nu}$ ($\mu \neq \nu$, $\mu=1, 2, \ldots, 7$, $\nu=1, 2, \ldots, 7$) of elements of said 42 intermediate element group $G_{\mu,\nu}^2$ calculated by said double desensitization means C15B are memorized over each shift time, which is regarded as that any one of the three values $-1, 0, +1$ is input (maintained) into the thirty elements of each said intermediate element group $G_{\mu,\nu}^2$ over shift time. In addition, in embodiment 1, the value of the 42 intermediate element group comprising thirty elements such as (+1,0,0,-1,+1, ... ,0), as said intermediate values, namely 1260(30×42=1260) values in total are memorized.

C17: Output Value Calculating Means

Output value calculating means C17 comprising connection weight memorizing means C17A, is a means to calculate the output values (values of output variables) over shift time based on said 42 intermediate values, namely the values $x_{\mu,\nu}^2$ ($\mu \neq \nu$, $\mu=1, 2, \ldots, 7$, $\nu=1, 2, \ldots, 7$) of said 42 intermediate variables which are input into said intermediate layer Nb.

As depicted in FIG. 5, said selective desensitization neutral network N in embodiment 1 comprises an output layer (output element group) Nc composed of 48 elements (output elements) which are connected with 1260 elements of said intermediate layer.

Said output layer Nc in embodiment 1 comprises six kinds of output element groups (the first output element group G13, the second output element group G23, ... , the six output element group G63), moreover, said six kinds of output element group $G_\gamma^3$ ($\gamma=1, 2, \ldots, 6$) comprise eight elements respectively (6×8=48).

Additionally, corresponding to the six kinds of output variables which are pre-set according to the six motions (the first output variable y1 corresponding to ⌈wrist flexion⌋, the second output variable y2 corresponding to ⌈wrist extension⌋, ... , the six output variable corresponding to ⌈wrist supination⌋) except ⌈neutral⌋, said six output element group $G_\gamma^3$ are pre-set in said output layer Nc as described in embodiment 1.

Accordingly, let the values of eight elements of each output element group $G_\gamma^3$ be $y_1^\gamma, y_2^\gamma, \ldots, y_6^\gamma$, each output variable $y_\gamma$ can be expressed as given in the following equation (15).

$$y_\gamma = (y_1^\gamma, y_2^\gamma, \ldots, y_6^\gamma) \quad \text{equation (15)}$$

In embodiment 1, the value $y_i^\gamma$ ($i=1, 2, \ldots, 8$) of elements of the six output element group $G_\gamma^3$ are calculated based on the values of said 1260 intermediate elements $x_j^{\mu,\nu}$ ($j=1, 2, \ldots, 30$) of said intermediate layer Nb as well as each of the 1260 pre-set values of connection weights corresponding to the importance of each value of said $x_j^{\mu,\nu}$.

Here, if each value of said connection weight corresponding to said $x_j^{\mu,\nu}$ is $\omega_{\gamma ij}^{\mu,\nu}$, and the pre-set threshold value corresponding to the element value $y_i^\gamma$ of said output element group $G_1^3$ is $h_i^\gamma$, when h is defined as a two-valued function where it takes a value of +1 as output value if the input value is over 0, whereas it takes an value of 0 as output value if the input value is below, the element value $y_i^\gamma$ of said output element group $G_i^3$ can be expressed as given in the following equation (16).

[Mathematic expression 1]

$$y_i^\gamma = h\left(\sum_{\mu,\nu(\neq\mu)} \sum_{j=1}^n \omega_{\gamma ij}^{\mu,\nu} x_j^{\mu,\nu} - h_i^\gamma\right) \quad \text{equation (16)}$$

That is to say, with their respective connection weights, the 48 elements of said output layer Nc in embodiment 1 are connected with the 1260 elements of said intermediate layer. Consequently, the element value $y_i^\gamma$ of said output layer Nc is a value (either of 0 and +1) calculated according to combination of the product of 1260 values of the intermediate elements $x_j^{\mu,\nu}$ and their connection weight $\omega_{\gamma ij}^{\mu,\nu}$ $\{x_i^{\mu,\nu} \times \omega_{\gamma ij}^{\mu,\nu}\}$.

As a result, the value of six output variable $y_\gamma$ in embodiment 1 namely said output value can be expressed as a eight-dimensional vector (two valued pattern) such as (0,+1,+1,0,+1,0,0,0) with the two values of 0, +1 as vector components.

C17A: Connection Weight Memorizing Means

Connection weight memorizing means C17A comprising a threshold value memorizing means C17A1 that memorizes the 48 threshold values $h_i^\gamma$, is a means to memorize the values of 1260 connection weights $\omega_{\gamma ij}^{\mu,\nu}$ corresponding to the values of 1260 intermediate elements $x_j^{\mu,\nu}$ of said intermediate layer with regard to the 48 elements of said output layer Nc. That is to say, said connection weight memorizing means C17A memorizes totally the values of 60480 connection weights $\omega_{\gamma ij}^{\mu,\nu}$ (1260×48=60480). What is more, it memorizes the values of said 60480 connection weights $\omega_{\gamma ij}^{\mu,\nu}$ trained by the below-mentioned connection weight training means C23, as well as said 48 threshold values $h_i^\gamma$ as described in embodiment 1.

C18: Output Value Memorizing Means

Output Value Memorizing(output value input) Means C18 is a means to memorize the values of said six output variables $y_\gamma$ ($\gamma=1, 2, \ldots, 6$) calculated by said output Value calculating Means C17. As described in embodiment 1, the element values $y_i^\gamma$ of said six output element group $G_\gamma^3$ ($\gamma=1, 2, \ldots, 6$) are memorized over shift time by way of the output value memorizing means C18, which is regarded as that either one of the two values 0,+1 is input (maintained) into the eight elements of each said output element group $G_\gamma^3$ over shift time. In addition, in embodiment 1, the values of the six output element group comprising eight elements such as (0, +1, +1, 0, +1, 0, 0, 0), namely 48(4×8=48) values in total are memorized as said output values.

C19: Correspondence Relationship Information Memorizing Means

The correspondence relationship information memorizing means C19 is a means to memorize the correspondence relationship information T that specifies the correspondence relationship between the six motions except ⌈neutral⌋ (a plurality of classification information and a plurality of events as the classification objects) and the values of output variable $y_\gamma$ (γ=1, 2, ..., 6) (value of output variables corresponding to each classification information as well as that corresponding to each event) pre-measured for each of said motions. The correspondence relationship information T in embodiment 1 refers to the information (correct motion information, correct motion data, teacher signals, dictionary information) regarding to the pre-measured values (ideal value) of the elements $py_1^\gamma$, $py_2^\gamma$, $py_8^\gamma$ of the six output element group $G_\gamma^3$ corresponding to the actual six motions. More specifically, the consecutive (ajacent) four elements, namely, five firing patterns of (+1, ..., +1, 0, ..., 0), (0, +1, ..., +1, 0, 0, 0), (0, 0, +1, ..., +1, 0, 0), (0, 0, 0, +1, ..., +1, 0) (0, ..., 0, +1, ..., +1), are pre-set to be +1.

Figure 7:
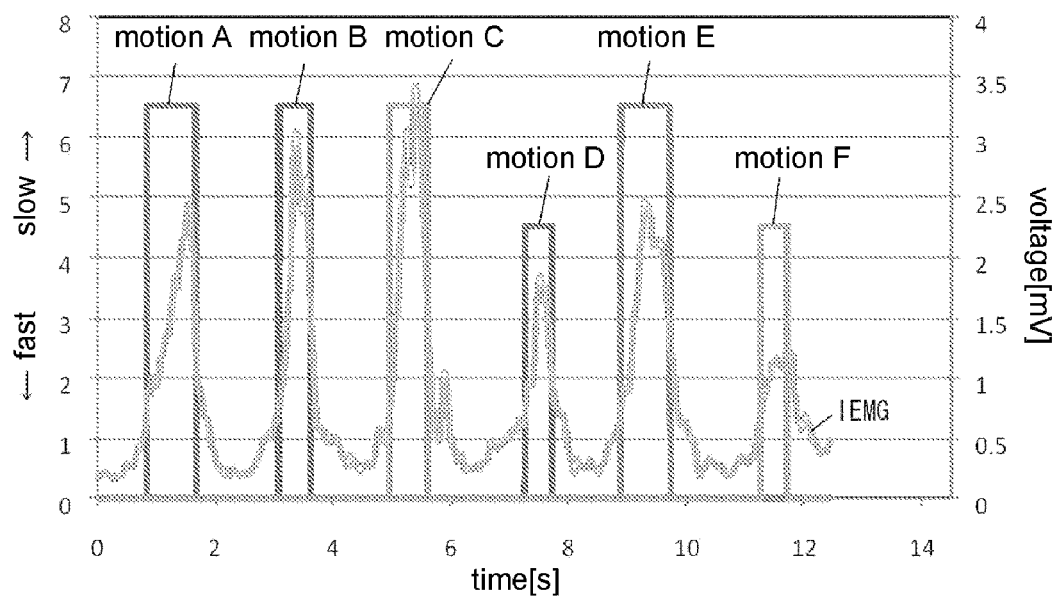
FIG. 7 illustrates the correspondence relationship information in embodiment 1 of the present invention, wherein vertical axis represents voltage [mV] and the horizontal axis represents time [s]; it illustrates the sum of the error eliminated values of the average integrated values and the scope of motion classification when six types of motions are actually performed in sequential order.

FIG. 7 illustrates the correspondence relationship information in embodiment 1 of the present invention, wherein vertical axis represents voltage [mV] and the horizontal axis represents time [s]; it illustrates the sum of the error eliminated values of the average integrated values and the scope of motion classification when six motions are actually performed in sequential order.

Here, as described in FIG. 7 of embodiment 1, in order to memorize said correspondence relationship information T, the sum A I EMGall (p) of said six average integrated values (v1~v6) after error being eliminated are calculated while the motions in the order from ⌈motion A⌋ to ⌈motion F⌋, namely in the order of ⌈wrist flexion⌋, ⌈wrist extension⌋, ⌈hand grasp⌋, ⌈hand extension⌋, ⌈wrist supination⌋, ⌈wrist pronation⌋ are actually performed by said subject at an interval of two seconds. Next, the threshold value for motion classification based on said sum A I EMGall (p) is decided because of errors accompanied to the motions at two second interval for said subject.

Specifically, if the pre-set sum threshold is th, and the pre-set ratio regarding the maximum A I EMGamax of said sum A I EMGall (p) is α(0<α<1), then the value of said sum threshold th and the maximum A I EMGamax multiplied by said ratio α (α×A I EMGamax) is determined as the threshold for motion classification. Moreover, in embodiment 1, said sum threshold is pre-set to be 0.2 [mV].

Next, based on said sum A I EMGall (p) and each of said threshold value th, (α×A I EMGamax), the pre-measured motions are classified. Specifically, if the six classification functions are represented by $M_1(p)$, $M_2(p)$, ..., $M_6(p)$, wherein the output for the six motions from ⌈motion A⌋ to ⌈motion F⌋ is +1 if classified, and 0 if not classified, each value of the classification functions $M_{m'}(p)$ (m'=1, 2, ..., 6) can be calculated by the following equations (17).

$$M_{m'}(p) = h(AIEMG_{all}(p) - th) \times h(AIEMG_{all}(p) - \alpha \times AIEMG_{amax})$$

equation (17)

That is to say, as described in FIG. 7, classification process is repeated wherein ⌈motion A⌋ is classified at the initial two seconds (0[s]~2[s]) by the first classification function M1($p$), and ⌈motion B⌋ is classified at the next two second (2[s]~4[s]) by the second classification function M2($p$), and then ⌈motion F⌋ is classified at the final two second (10[s]~12[s]) by the six classification function M6($p$).

Next, said classification function Mm'(p), (m'=1, 2, ..., 6) takes the frame number (sequential frame number) obtained following the value of +1 as the pseudo velocity of motions. After that, the six motions at two second interval of said subject are repeated for a plurality of times, normalization of motion velocity is carried out based on the maximum value of said sequential frame number. More specifically, let said sequential frame number be Wm', the maximum of said sequential frame number be $W_{m'max}$, and the normalized motion velocity be $N_{sp}$ (p), the normalized motion velocity $N_{sp}(p)$ can be expressed as given by the following equations (18).

$$N_{sp}(p) = W_m / W_{m'max}$$ equation (18)

Besides, similar to said input values $N_i$ (p), $N_a$ (p), $N_d$ (p), the normalized motion velocity $N_{sp}(p)$ (0≤$N_{sp}$ (p)≤1) is converted respectively to enable a vector expression (two valued pattern) with the four values of +1 and four 0 as vector components. More specifically, the correspondence between said normalized motion velocity $N_{sp}(p)$ and five pattern vector expression of said ideal value $py_i^\gamma$ (i=1, 2, ..., 8) can be decided by the following equations (19-1)~(19-5).

if 0≤$N_{sp}$ (p)≤0.2:

$N_{sp}(p) = (0, ..., 0, +1, ..., +1)$  equation (19-1)

if 0.2≤$N_{sp}(p)$ 0.4:

$N_{sp}(p) = (0, 0, 0, +1, ..., +1, 0)$  equation (19-2)

if 0.4≤$N_{sp}(p)$≤0.6

$N_{sp}(p) = (0, 0, +1, ..., +1, 0, 0)$  equation (19-3)

if 0.6≤$N_{sp}(p)$≤0.8

$N_{sp}(p) = (0, +1, ..., +1, 0, 0, 0)$  equation (19-4)

if 0.8≤$N_{sp}(p)$≤1

$N_{sp}(p) = (+1, ..., +1, 0, ..., 0)$  equation (19-5)

C20: Motion Classification Means the motion classification means (an operational decision estimating means, an event type estimating means, an classification information estimating means) C20 comprising a motion type classification means C20A, and a motion velocity classification means C20B, is a means to classify the motions (estimate operational decision, estimate event type, estimate type classification information) of said subject based on said correspondence relationship information T pre-stored by said correspondence relationship information means C19 and the values of said six output variables $y_\gamma$.

C20A: Motion Type Classification Means motion type classification means (type information estimating means) C20A is a means to classify any one of the seven types of motions (⌈neutral⌋, ⌈wrist flexion⌋, ⌈wrist extension⌋, ⌈hand grasp⌋, ⌈hand extension⌋, wrist supination, ⌈wrist pronation⌋) (estimate the type information on the types of motions).

As described in said motion type classification means C20A of embodiment 1, because four elements fire consecutively, if there exists said output element group $G_\gamma^3$ (γ=1, 2, ..., 6) having three firing elements which fire consecutively subsequent to the pre-set classification frame number Ps, the five patterns, as said correspondence relationship T shown by said equations (19-1)~(19-5), are classified as the motions corresponding to said output element group $G_\gamma^3$ (γ=1, 2, ..., 6). For instance, when said output element group $G_\gamma^3$ gets (0, +1, +1, 0, +1, 0, 0, 0) subsequent to the classification frame number Ps, it is classified as ⌈wrist pronation⌋. In addition, if there does not exist said output element group $G_\gamma^3$ (γ=1, 2, ..., 6) having three firing elements which fire consecutively subsequent to the pre-set classification frame number Ps, it is classified as ⌈neutral⌋. Besides, in embodiment 1, if there exist a plurality of said output element group $G_\gamma^3$ having three firing elements which fire consecutively subsequent to the pre-set classification frame number Ps, it is classified as that a plurality of corresponding motions are performed simultaneously. Accordingly, let the frame number be $p_\gamma$ ($\gamma$=1, 2, . . . , 6, 0≤$p_\gamma$≤Ps) where more than three elements of six output element group $G_\gamma^3$ fire consecutively, if $p_\gamma$=Ps, by means of the classification means C20A, it is classified as the motions corresponding to said output element group $G_\gamma^3$; if no output element group $G_\gamma^3$ exists which satisfies the equation $p_\gamma$=Ps, it is classified as ﹁neutral﹂.

C20B: Motion Velocity Classification Means

Motion velocity classification means (velocity information estimating means, force information estimating means) C20B is a means to classify the velocity of said six motions performed except ﹁neutral﹂ (to estimate velocity information of each motions). As described in embodiment 1, said motion velocity classification means C20B is applied to classify velocity of said motions by comparing the values converted numerically from the firing pattern of elements of said output element group $G_\gamma^3$ ($\gamma$=1, 2, . . . , 6) corresponding to specific motions classified by said motion classification means C20A, and the values converted numerically the five patterns expressed by said equations (19-1)~(19-5). More specifically, weights of 1th to eighth are applied on specified 1th to eighth elements of said output element group $G_\gamma^3$, then the value of 1th to eighth elements $y_i^\gamma$ (i=1, 2, . . . , 6) is multiplied by the weights of 1th to $8^{th}$, the value obtained is further divided by the firing element number to obtain the classification value.

For instance, when the first output element group G13 (0,+1,+1,0,+1,0,0,0) which is classified as ﹁wrist pronation﹂ is (0,+1,+1,0,+1,0,0,0), said classification value is 3.3({(0×1)+(+1×2)+(+1×3)+(0×4)+(+1×5)+(0×6)+(0×7)+(0×8)}/3= (2+3+5)/3=10/3=3.3). Besides, said classification value of the five patterns expressed by said equations (19-1)~(19-5) is calculated to be 2.5((1+2+3+4)/4=2.5) to 6.5((5+6+7+8)/4=6.5).

Subsequently, velocity is classified by determining where the calculated average value of said classification value over said classification frame number Ps is located within said classification value range (2.5~6.5) of the five patterns expressed by said equations (19-1)~(19-5). As described in embodiment 1, if $d_\gamma$ ($p_\gamma$)($\gamma$=1, 2, . . . , 6, $p_\gamma$=1, 2, . . . , Ps) represents the classification value of a specific output element group $G_\gamma^3$ over frame time, and $d_\gamma$ ($\gamma$=1, 2, . . . , 6, and $d_\gamma$={$d_\gamma$(1)+$d_\gamma$(2)+ . . . +$d_\gamma$(Ps)}/Ps) represents the average of said the classification value $d_\gamma$ (p$\gamma$), if 2.5≤$d_\gamma$≤3.5, it is classified as ﹁fast﹂, if 3.5≤$d_\gamma$≤5.5, it is classified as ﹁medium﹂, and if 5.5≤$d_\gamma$≤6.5, it is classified as ﹁slow﹂.

Furthermore, as shown in embodiment 1, motion velocity is classified, since force is generated corresponding to the change of velocity, information such as the force of motion (force information, ﹁strong﹂, ﹁medium﹂, ﹁weak﹂) can also be estimated corresponding to motion velocity (velocity information, ﹁fast﹂, ﹁medium﹂, ﹁slow﹂).

More specifically, similar to the case with velocity classification, with regard to said average value $d_\gamma$ corresponding to a specific motion, which represents the firing patterns of elements of the output element group $G_\gamma^3$ ($\gamma$=1, 2, . . . , 6), the force of motion can be classified by determining the range of $d_\gamma$, if 2.5≤$d_\gamma$≤3.5, it is classified as ﹁strong﹂, if 3.5≤$d_\gamma$≤5.5, it is classified as ﹁medium﹂, and if 5.5≤$d_\gamma$≤6.5, it is classified as ﹁slow﹂.

In this case, the force of motion can be classified even when the actual motion velocity is 0. For instance, in the state of ﹁grasped a hand(motion C)﹂, if the subject changed grasping force from ﹁weak﹂ to ﹁strong﹂, when said average value $d_3$, representing the firing patterns of elements of the third output element group $G_3^3$, changes from the range 5.5≤$d_3$≤6.5 to 2.5≤$d_3$≤3.5, it can be classified that motion force changes from ﹁weak﹂ to ﹁strong﹂. Additionally, for instance, it is possible to estimate the type and force of motions regarding to the operational decision of a lost limb of a disabled. For example, similar to embodiment 1, regarding a subject without a hand, by measuring the surface EMG signals obtained from the six EMG sensors SN1~SN6 attached on said six measuring positions on the wrist of said subject, the surface EMG signals change with the operational decision of said subject, thus said average value $d_\gamma$ changes, hence from operational decision of a subject, the type and force of motions which the lost hand intended to perform can be estimated.

Moreover, as described in embodiment 1, while there are three categories in motion velocity (velocity information): ﹁fast﹂, ﹁medium﹂, ﹁slow﹂, any one of the three categories in the force of motion (force information ﹁strong﹂, ﹁medium﹂, ﹁weak﹂) can be estimated simultaneously with motion velocity.

Figure 8:
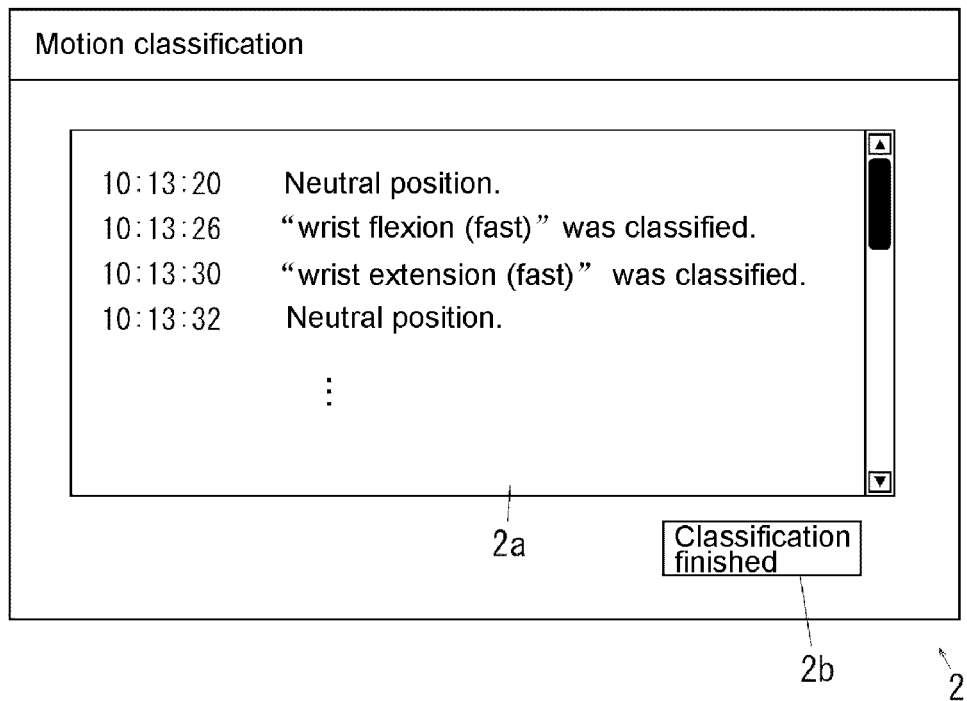
FIG. 8 illustrates motion classification image in embodiment 1 of the present invention.

FIG. 8 illustrates motion classification image in embodiment 1 of the present invention;

C21: motion classification image display means (operational decision display means, event display means, categorization information display means) C21 is a means to display motion classification image 2 (operational decision estimating means, event estimating means, categorization information estimating means), as shown in FIG. 8, illustrating the motions of said subject (estimated operational decision of a subject, estimated events, estimated categorization information) classified by said motion classification means C20. In FIG. 8, said motion classification image 2 comprises a display segment 2a, which illustrates the classified start time, type as well as velocity of said subject's motion; and a motion classification stop button 2b to stop motion classification of said subject. Said motion classification image display means C21 in embodiment 1 illustrates the classified start time, type as well as velocity of said motion in said display segment 2a.

C22: Motion Classification Stop Determining Means

Motion classification stop determining means C22 is a means to determine whether motion classification of said subject has finished or not. By way of said motion classification stop determining means C22 in embodiment 1, whether or not the motion classification of said subject has finished is determined by whether select said motion classification stop button 2b or not.

C23: Connection Weight Training Means

Connection weight learn training means C23, having a threshold value training means C23A and an initial value setting means C23B, is a means, based on difference between the seven motions (estimated operational decision of a subject, estimated event, estimated categorization information) that are classified by said motion classification means C20, and the pre-measured actual motions (actual operational decision, actual event, actual categorization information) to train each of said connection weights by updating said connection weights. As described in embodiment 1, by way of said connection weight training means C23, after the motion classification being determined as finished by said motion classification stop determining means C22, the values of said 60480 connection weights, $\omega_{\gamma ij}^{\mu,\nu}$, are updated according to the following equation (20-1). In addition, let c denote the pre-set positive constant (0<c<1, for example c=0.3), then $\omega_{\gamma ij}^{\mu,\nu}$ can be decided as follows, $$\omega_{\gamma ij}^{\mu,\nu} \leftarrow \omega_{\gamma ij}^{\mu,\nu} + c(py_i^\gamma - y_i^\gamma) \times (x_j^{\mu,\nu}) \qquad \text{equation (20-1)}$$

C23A: Threshold Value Training Means

Threshold value training means C23A is a means, after motion classification of said subject being determined as finished, to train said threshold values $h_i^\gamma$ according to the following equation (20-2) by updating said 48 threshold values.

$$h_i^\gamma \leftarrow h_i^\gamma - c(py_i^\gamma - y_i^\gamma) \qquad \text{equation (20-2)}$$

C23B: Initial Value Setting Means

The initial value setting means C23B is a means to set the initial values of said 60480 connection weights $\omega_{\gamma ij}^{\mu,\nu}$ as well as said 48 threshold values $h_i^\gamma$. As described in embodiment 1, the initial value setting means C23B is applied to set said initial values based on the measured values which are calculated from inputting said six average integrated values ($v_1 \sim v_6$) into said selective desensitization neutral network while setting said ideal value $py_i^\gamma$ regarding said correspondence relationship information memorizing means C19, namely the values of said intermediate variables $x_{\mu,\nu}$ ($\mu \neq \nu$, $\mu=1, 2, \ldots, 7, \nu=1, 2, \ldots, 7$), and the values of said six output variables $y_\gamma$ ($\gamma=1, 2, \ldots, 6$). More specifically, with regard to the six motions at two second interval as shown in FIG. 7, said connection weights $\omega_{\gamma ij}^{\mu,\nu}$ as well as said threshold values $h_i^\gamma$ are trained in order for the output value of frame number subsequent to the value of +1 of each of said classification function Mm'(p) (m'=1, 2, ..., 6) to become said ideal value $py_i^\gamma$.

For instance, in case that ⌈motion A⌋ at the initial two second (0[s]~2[s]) is ⌈fast⌋, for the values of the eight elements in the first output element group $G_1^3$, if $(y_1^1, y_2^1, \ldots, y_8^1) = (py_1^1, py_2^1, \ldots, py_8^1) = (0, \ldots, 0, +1, \ldots, +1)$ is true, then for the values of the eight elements of other output element group $G_\gamma^3$ ($\gamma=2, \ldots, 6$), $(y_1^\gamma, y_2^\gamma, \ldots, y_8^\gamma) = (0, 0, \ldots, 0)$ is regarded to be also true.

In this case, when the values $x_j^{\beta,\nu}$ of the 1260 elements of said intermediate layer Nb are obtained by double desensitization according to said equation (13)', if $\omega_{\gamma ij}^{\mu,\nu}$ a=$h_i^\gamma$=0, and c=0.3, for the measured values of the eight elements in the first output element group $G_1^3$, because $(y_1^1, y_2^1, \ldots, y_8^1)=(0, 0, \ldots, 0)$, substitute the equation into said equations (20-1) and (20-2), the 10080 (1260×8) connection weight $\omega_{1\gamma ij}^{\mu,\nu}$ and the eight threshold values $h_i^1$ for the eight elements in the first output element group $G_1^3$ can be trained as shown in the following equations (20-1-1) and (20-2-1).

$$\Omega_{1\gamma ij}^{\mu,\nu} \leftarrow 0 + 0.3 \times (py_i^1 - 0) \times (x_j^{\mu,\nu}) \qquad \text{equation (20-1-1)}$$

$$h_i^1 \leftarrow 0 - 0.3 \times (py_i^1 - 0) \qquad \text{equation (20-2-1)}$$

Accordingly, since $py_1^1$=0, the 1260 connection weights $\omega_{11j}^{\mu,\nu}$ corresponding to the first element of the first output element group $G_1^3$ are not updated, neither the threshold value $h_1^1$ corresponding to said first element ($\omega_{11j}^{\mu,\nu}$=0, $h_1^1$=0) are updated. In addition, since $py_8^1$=1, if $x_.$=1, the 1260 connection weights $\omega_{18j}^{\mu,\nu}$ corresponding to the eighth element are updated to be 0.3, and the threshold value $h_8^1$ corresponding to said eighth element is updated to be −0.3 ($\omega_{18j}^{\mu,\nu}$=0.3, $h_8^1$=0.3).

Furthermore, with regard to each motion (from ⌈motion B⌋ to ⌈motion F⌋) performed at the subsequent every two seconds, said connection weights $\omega_{\gamma ij}^{\mu,\nu}$ and said threshold values $h_i^\gamma$ can be learn in the same way.

Thus, said 60480 connection weights $\omega_{\gamma ij}^{\mu,\nu}$ as well as said 48 threshold values $h_i^\gamma$ can be set as said initial values through repeated test training (measurement) in order to regularize motion velocity. Moreover, said connection weights $\omega_{\gamma ij}^{\mu,\nu}$ as well as said threshold values $h_i^\gamma$ are memorized by said connection weight memorizing means C17A as said initial values.

(Description of Flow Chart in Embodiment 1)

Next, the flow of processing of the function approximation program of control unit is described by flow chart in embodiment 1. In addition, with regard to setting up said correspondence relationship information T and the initial values of said 60480 connection weights $\omega_{\gamma ij}^{\mu,\nu}$ as well as said 48 threshold values $h_i^\gamma$, when measurement of six motions is carried out on said subject at two second interval, the ideal values as well as the initial values are only calculated to be memorized according to said equations (17), (18), (19-1)~(19-5), (20-1) and (20-2), hence a detailed description of the flowchart is omitted.

(Description of Flow Chart for Motion Classification in Embodiment 1)

Figure 9:
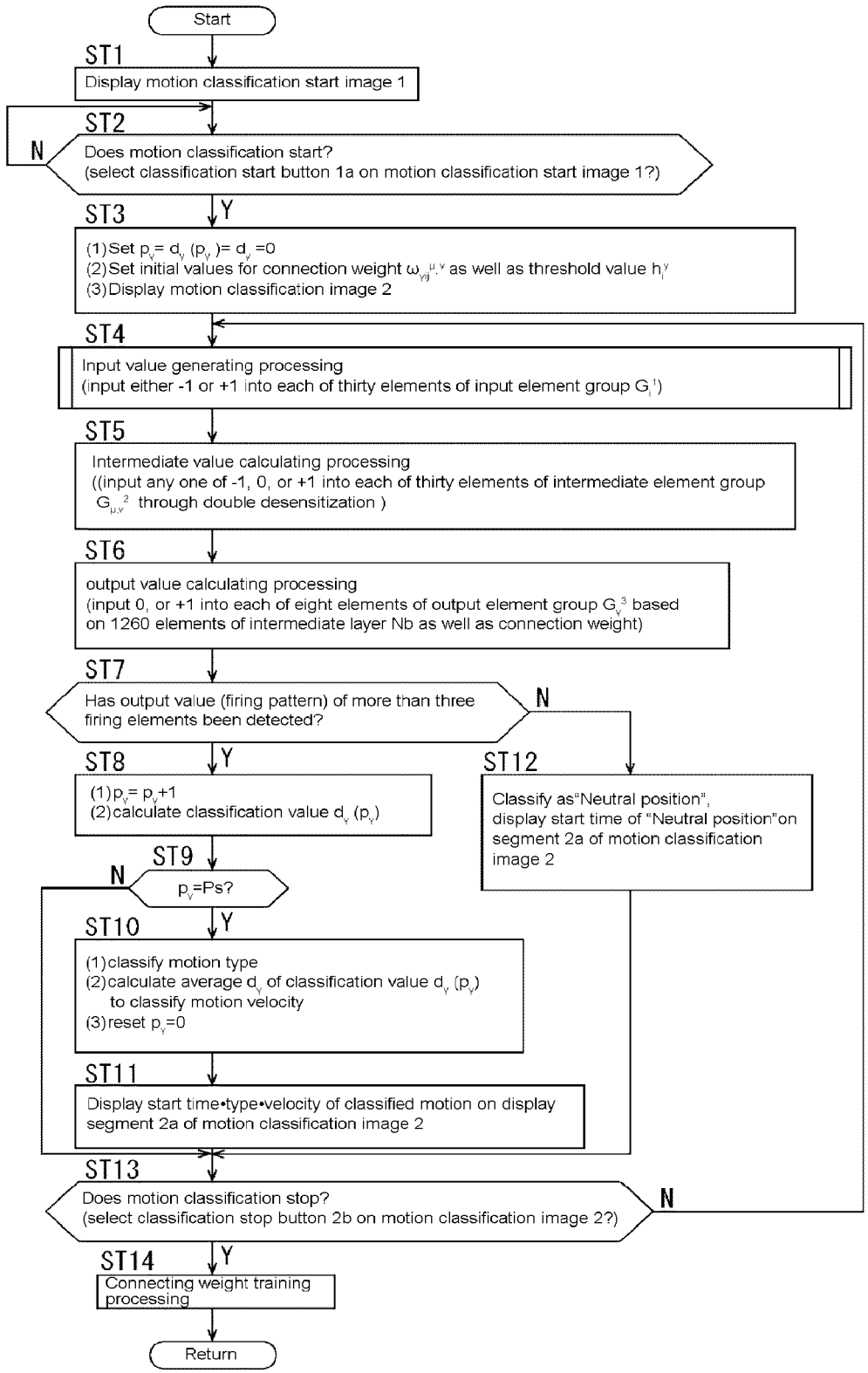
FIG. 9 is a flowchart of motion classification process of the motion classification program in embodiment 1 of the present invention.

FIG. 9 is a flowchart of motion classification process of the motion classification program in embodiment 1 of the present invention;

As described in the flow chart in FIG. 9, the processing of each ST (step) is carried out according to programs memorized in ROM etc of said control unit C. Additionally, the processing is carried out with multitasking alongside other processing of the control unit C.

FIG. 9 shows a flowchart in which when the power for said surface EMG signals Measuring apparatus U1 as well as said classification client personal PC is turned on, said classification program AP1 starts after booting.

In ST1 of FIG. 9, the motion classification start image 1 shown in FIG. 6 is displayed by display H2, and then move to ST2.

In ST2, by determining whether or not to select the classification start button 1a of the motion classification start image 1, whether or not the start classification of six motions of a subject, as shown in FIG. 2, is determined. If yes (Y), then move to ST3, if no (N), then return to ST2.

In ST3, the following process (1)~(3) are carried out, then move to ST4.
(1) Set the six subsequent frame numbers $p_\gamma$ ($\gamma=1, 2, \ldots, 6$), (6×$p_s$) classification value $d_\gamma(p_\gamma)$ ($\gamma=1, 2, \ldots, 6$, $p_\gamma=1, 2, \ldots, p_s$), six average value $d_\gamma$ ($\gamma=1, 2, \ldots, 6$) as 0 ($p_\gamma$=$d_\gamma$)($p_\gamma$)=0).
(2) Set the initial values of the 60480 connection weights $\omega_{\gamma ij}^{\mu,\nu}$ ($\gamma=1, 2, \ldots, 6$, i=1, 2, ..., 8, j=1, 2, ..., 8, $\mu \neq \nu$, $\mu=1, 2, \ldots, 7, \nu=1, 2, \ldots, 7$) as well as said 48 threshold values $h_i^\gamma$ ($\gamma=1, 2, \ldots, 6$, i=1, 2, ..., 8).
(3) Display the motion classification start image 2 shown in FIG. 8 by display H2.

Figure 10:
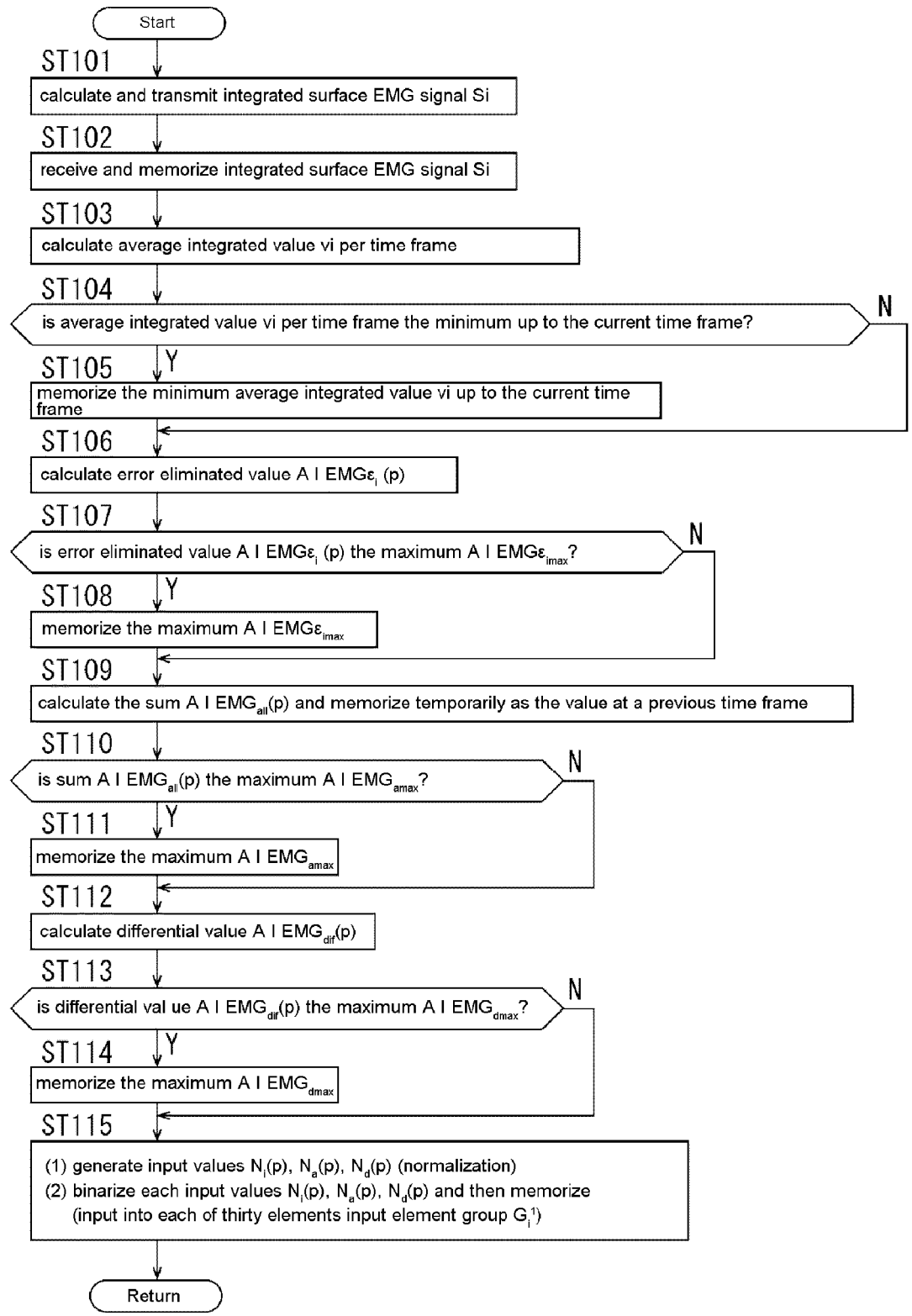
FIG. 10 is a flowchart of input value generating process of the motion classification program in embodiment 1 of the present invention.

In ST4, the below mentioned input value generating processing shown in FIG. 10 is carried out to generate the value of eight input variables $x_i$ (i=1, 2, ..., 8) (input value). That is to say, either −1 or +1 is input into the thirty elements of the eight input element groups $G_i^1$(i=1, 2, ..., 8), namely 240 (8×30=240) elements (to memorize the 240 values of (+1, −1)). And then move to ST5.

In ST5, the double desensitization shown by equation (13)' is carried out, and the values of the 42 intermediate variables $x_{\mu,\nu}$ ($\mu \neq \nu$, $\mu=1, 2, \ldots, 7, \nu=1, 2, \ldots, 7$) (intermediate value) are calculated. That is to say, either −1, 0, or +1 is input into the thirty elements of the 42 input element groups $G_{\mu,\nu}^2$ ($\mu \neq \nu$, $\mu=1, 2, \ldots, 7, \nu=1, 2, \ldots, 7$), namely 1260 (42×30=1260) elements (to memorize the 1260 values of (+1, 0, −1)). And then move to ST6.

In ST6, as shown in equation (16), the sum value to add up all the results of products of the values of 1260 elements of the intermediate layer Nb, $x_{.(j=1, 2, \ldots, 8, \mu \neq \nu, \mu=1, 2, \ldots, 7, \nu=1, 2, \ldots, 7)}$ and the connection weights $\omega_{\gamma ij}^{\mu,\nu}$ is filtered with threshold value $h_i^\gamma$ to calculate six output variables $y_\gamma$ (output value). That is to say, either 0 or +1 is input into the eight elements of the six input element groups $G_\gamma^3$ ($\gamma=1, 2, \ldots, 6$), namely totally 48 (6×8=48) elements (to memorize the 48 values of (0, −1)). And then move to ST7.

In ST7, it is determined whether an output element group $G_\gamma^3$ (value of output variable $y_\gamma$, output value, firing pattern) having more than three firing elements has been detected or not. If the result is yes (Y), then move to ST8, if no (N), then return to ST12.

In ST8 the following processes (1),(2) are carried out, then move to ST9.
(1) Add +1 to subsequent frame number $p_\gamma$. ($p_\gamma=p_\gamma+1$)
(2) Calculate classification value $d_\gamma(p_\gamma)$.

In ST9, it is determined whether subsequent frame number $p_\gamma$ equals to classification frame number or not. If the result is yes (Y), then move to ST10, if no (N), then return to ST13.

In ST10, the following processes (1)~(3) are carried out, then move to ST11.
(1) Classify motion types corresponding to the output element group $G_\gamma^3$ if the subsequent frame number $p_\gamma$ takes on the value of classification frame number Ps.
(2) Classify motion velocities by calculating the average $d_\gamma$ of the classification values $d_\gamma(p_\gamma)$ of the output element group $G_\gamma^3$ corresponding to the classified motions, ($d_\gamma=d_\gamma(1)+d_\gamma(2)+ \ldots +d_\gamma(2)/Ps$). That is to say, if $2.5 \leq d_\gamma \leq 3.5$, it is classified as ⌈fast⌋, if $3.5 \leq d_\gamma \leq 5.5$, it is classified as ⌈medium⌋, and if $5.5 \leq d_\gamma \leq 6.5$, it is classified as ⌈slow⌋.
(3) Set the subsequent frame number $p_\gamma$ as 0 ($p_\gamma=0$) if it reaches the classification frame number Ps.

In ST11, the classified motion start time, type, velocity are displayed (recorded) on the display segment 2a of motion classification image 2, then move to ST13.

In ST12, the upper wrist of a subject is classified as ⌈neutral⌋ position, the start time of ⌈neutral⌋ position is displayed (recorded) on the display segment 2a of motion classification image 2, then move to ST13.

In ST13, by determining whether or not to select the classification stop button 2b of the motion classification image 2, it is determined whether or not to stop motion classification of a subject. If the result is yes (Y), then move to ST14, if no (N), then return to ST4.

In ST14, the connection weight learning processing shown by equations (20-1), (20-2) is carried out, and the values of 60480 connection weights $\omega_{\gamma ij}^{\mu\text{-}\nu}$ as well as 48 threshold values $h_i^\gamma$ are trained (updated), then move back to ST1.

(Description of Flow Chart for Input Value Generating Processing in Embodiment 1)

FIG. 10 is a flowchart of input value generating processing of the motion classification program in embodiment 1 of the present invention.

As described in the flow chart in FIG. 10, the processing of each ST (step) is carried out according to programs memorized in ROM etc of said control unit C. Additionally, the processing is carried out with multitasking alongside other processing of the control unit C.

FIG. 10 shows a flowchart in which when the power supply for said surface EMG signals Measuring apparatus U1 as well as said classification client personal PC is turned on, said classification program AP1 starts after booting.

As shown in ST101 of FIG. 10, the signals Measuring apparatus U1 calculates the integrated surface EMG signals (s1~s6) which are the integrated values of surface EMG signals measured on the six surface EMG sensors SN1~SN6 shown in FIG. 1, then send to classification client personal PC. Then move to ST102.

In ST102, the classification client personal PC memorizes the received integrated surface EMG signals (s1~s6). Then move to ST103.

In ST103, as shown by equations (2-1), (2-2) and FIG. 4, the average integrated values (v1~v6), which are the average value of the six integrated surface EMG signals (s1~s6) per time frame, A I $\text{EMG}_i$ (p) (i=1, 2, …, 6, p=1, 2, …), are calculated. Then move to ST104.

In ST104, as shown by equation (3), whether or not the calculated six average integrated values vi per frame time, A I $\text{EMG}_i$ (p), are the minimum $\epsilon i$ up to the current time frame (p-th frame), is determined respectively. If the result is yes (Y), then move to ST105, if no (N), then move to ST106.

In ST105, the minimum ($\epsilon 1$~$\epsilon 6$) of the average integrated values (v1~v6) that are determined are memorized respectively. Then move to ST106.

In ST106, as shown by equation (4), by deducting, as errors, the six minimums $\epsilon i$ from the six average integrated values vi per time frame, A I $\text{EMG}_i$ (p), the error eliminated value A I $\text{EMG}\epsilon_i$ (p) (i=1, 2, …, 6, p=1, 2, …), are calculated. Then move to ST107.

In ST107, as shown by equations (7-1), whether or not the calculated six error eliminated value A I $\text{EMG}\epsilon_i$ (p), is the maximum A I $\text{EMG}\epsilon_{imax}$ (p) up to the current frame time (p-th frame), is determined respectively. If the result is yes (Y), then move to ST108, if no (N), then move to ST109.

In ST108, the maximum A I $\text{EMG}\epsilon_{imax}$ (p) of the error eliminated value A I $\text{EMG}\epsilon_i$ (p) that are determined are memorized respectively. Then move to ST109.

In ST109, the sum, A I $\text{EMG}_{all}$ (p) (p=1, 2, …), of the six error eliminated value A I $\text{EMG}\epsilon_i$ (p) is calculated, and temporarily memorized as the sum value A I $\text{EMG}_{all}$ (p) of the previous time frame in order to calculate the differential value A I $\text{EMG}_{dif}$(p+1) at the next frame. Then move to ST110.

In ST110, as shown by equations (7-2), whether or not the calculated sum value A I $\text{EMG}_{all}$ (p), is the maximum A I $\text{EMG}\epsilon_{amax}$ up to the current frame time (p-th frame), is determined. If the result is yes (Y), then move to ST111, if no (N), then move to ST112.

In ST111, the maximum A I $\text{EMG}\epsilon_{amax}$ of the sum value A I $\text{EMG}_{all}$ (p) that are determined are memorized. Then move to ST112.

In ST112, as shown by equation (6), the differential value A I $\text{EMG}\epsilon_{dif}$(p) of the sum value A I $\text{EMG}_{all}$ (p) at each time frame are calculated. Then move to ST113.

In ST113, as shown by equations (7-3), whether or not the calculated differential value A I $\text{EMG}_{dif}$(p) is the maximum A I $\text{EMG}_{dmax}$ up to the current frame time (p-th frame), is determined. If the result is yes (Y), then move to ST114, if no (N), then move to ST115.

In ST114, the maximum A I $\text{EMG}_{dmax}$ of the differential sum value A I $\text{EMG}_{dif}$(p) that are determined are memorized. Then move to ST115.

In ST115, the following processes (1),(2) are carried out, then return to ST101.
(1) calculate (generate)) eight input values $N_i$(p) (p=1, 2, …, 6), $N_a$(p), $N_d$(p) through normalization as shown by equations (8-1)~(8-3).
(2) either −1 or +1 is input into the 240 (8×30=240) elements (to memorize the 240 values of (−1, +1)) by memorizing the binarized eight input values $N_i$(p), $N_a$(p), $N_d$(p) as shown by equations (9-1)~(9-3). And then return to ST101.

Effect of Embodiment 1

After attaching six EMG sensors SN1~SN6 to the right wrist of a subject (refer to FIG. 1), said motion classification system S having said components start motion classification (refer to ST2 in FIG. 9) regarding to the seven motions (refer to FIG. 2) of a subject by selecting classification start button 1a (refer to FIG. 6) of motion classification start image 1.

Additionally, in said motion classification processing (refer to FIG. 9) of embodiment 1, the six surface EMG signals obtained from the six EMG sensors SNP~SN6 are converted to the input value $N_i(p)$ (p=1, 2, . . . , 6), $N_a(p)$, $N_d(p)$ of the selective desensitization neutral network N (refer to FIG. 5) at each shift time, and are input into the input layer Na of said selective desensitization neutral network N (refer to ST4 of FIG. 9, ST101~ST115 of FIG. 10). As a result, either −1 or +1 is input, at each shift time, into the thirty elements of the eight input element group $G_i^1$ (i=1, 2, . . . , 8), namely totally 240 (8×30=240) elements of the input layer Na of said selective desensitization neutral network N.

Moreover, in the intermediate layer Nb of said selective desensitization neutral network N, through double desensitization shown in equation (13)', any one of the three values −1,0,+1 is input, at each shift time, into the thirty elements of 42 intermediate element group $G_{\mu,\nu}^2$ (≠ν, μ=1, 2, . . . , 7, ν=1, 2, . . . , 7), totally 1260 elements (refer to ST5 of FIG. 9). In addition, either 0 or +1 is input into the eight elements of six output element group $G_\gamma^3$ (γ=1, 2, . . . , 6) (refer to ST6 of FIG. 9), totally 48 elements in the output layer Nc of said selective desensitization neutral network N according to equation (16). Subsequently, if there exists output element group $G_7^3$ having three firing elements which fired consecutively subsequent to the pre-set classification frame number Ps, in company with classification of motion types including ⌈wrist flexion⌋, ⌈wrist extension⌋, ⌈hand grasp⌋, ⌈hand extension⌋, ⌈wrist supination⌋, ⌈wrist pronation⌋ as well as velocities including ⌈fast⌋, ⌈medium⌋, ⌈slow⌋, if there exists no such output element group, the upper wrist of a subject is classified as ⌈neutral⌋ (refer to ST7~ST12 of FIG. 9). as a result, the start time, types, velocities are displayed on display segment 2a (refer to FIG. 8) on motion classification image 2 (refer to ST11 of FIG. 9).

Consequently, compared with the techniques described in said non-patent literatures 1 and 2, in which classification of a certain motion is only carried out at a constant velocity, said motion classification system S described in embodiment 1 enables classification of a certain motion at different velocity.

Moreover, motion classification is carried out by way of a selective desensitization neutral network N with high training ability (generalization ability) (for instance, refer to Kokai publication Patent Tokukai No. 2009-64216), thus, compared with the techniques described in said non-patent literatures 1 and 2, in which motion classification is carried out based on statistic approach, motion classification of a subject is expected to be carried out with less training.

In addition, as described in embodiment 1, eight input values $N_i(p)$, $N_a(p)$, $N_d(p)$ obtained by removing noise from six surface EMG signals that are measured by the six EMG sensors SNP~SN6, are input into the selective desensitization neutral network N according to said input value generating processing. Besides, because said input value generating processing enables generation of a sufficient number of input values $N_i(p)$, $N_a(p)$, $N_d(p)$ at each shift time [10 ms] with little calculation, said motion classification can be carried out without any delay.

With regard to the six input values Ni(p) corresponding to 6 ch EMG sensors SNP~SN6, because normalization is carried out in the range of 0 to 1, a plurality of input values $N_i(p)$ can have a uniform value even when different types and different velocities are carried out. For example, for the input values $N_i(p)$~$N_4(p)$ of the 1 ch~4 ch, it is possible for $N_1(p)=N_2(p)=N_3(p)=N_4(p)$. In this case, even though two types of input value $N_i(p)$ taking on the same value are modified mutually (Mutually selective Desensitization), it is quite possible that a plurality of the corresponding 12 intermediate element group $G_{\mu,\nu}^2$ (μ=1, 2, 3, 4, ν=1,2, 3,4, μ≠ν) takes on an uniform intermediate value. That is to say, it is quite possible to have the same three value pattern (for example, (+1,0,0,−1,+1, . . . ,0)) for different input values.

Besides, if a majority obtains an uniform three value pattern for different input values, the connection weight $\omega_{\gamma ij}^{\mu,\nu}$ for calculating output value also approximates an uniform value whenever training is performed (refer to equations (20-1), (20-2)). This circumstance is named as ⌈connection weight averaging according to one-to-many correspondence⌋, which is regarded as the reason for decreased training efficiency and classification accuracy.

In order to solve this problem, said sum $N_a(p)$ takes on the normalized sum value of the six input values $N_1(p)$~$N_6(p)$ including not only the input values that get uniform value (1 ch~4 ch), but also the input values that get different value (5 ch~6 ch), thus increases the possibility for said sum $N_a(p)$ to get different value from the input values ($N_1(p)$~$N_4$ p of 1 ch~4 ch) that get uniform value.

That is to say, said sum $N_a(p)$ entailing high possibility to get a value different from said six input values $N_i(p)$ is applied as input value.

In addition, said sum $N_a(p)$ is only used for double desensitization of the other seven input values $N_i(p)$, $N_a(p)$. Accordingly, said motion classification system S of embodiment 1, compared with selective desensitization neutral network in which selective desensitization is carried out just once only (single desensitization), can be expected to further decrease training while improve classification accuracy. In addition, compared with the case wherein double desensitization is not carried out, when double desensitization is carried out, like said motion classification system S of embodiment 1, it is confirmed by experiment etc that classification accuracy was improved by 20 percent.

EXPERIMENTAL EXAMPLES

Here, in order to find out whether high classification accuracy with little training can be achieved by carrying out said input value generating processing as well as said motion classification processing, the following experimental example is prepared.

Experimental Example 1

In said motion classification system S of example 1, equivalent components of said motion classification system S of embodiment 1 are prepared, then said input value generating processing (refer to FIG. 10) as well as said motion classification processing (refer to FIG. 9) of embodiment 1 are carried out. Furthermore, said 60480 connection weights $\omega_{\gamma ij}^{\mu,\nu}$ as well as said 48 threshold values $h_i^\gamma$ are determined when six motions are carried out twice respectively (two sets) on said subject at two second interval at three velocities of ⌈fast⌋, ⌈medium⌋, ⌈slow⌋. That is to say, 36 (6×3×2) sample data are trained.

Besides, in said motion classification system S of example 1, six motions at three velocities, namely totally 18 motions are classified by carrying out six time (six sets) for actual motion classification.

In addition, in experimental example 1, ⌈Personal-EMG⌋ of Oisaka Electronic Device Ltd is applied as Surface EMG Measuring apparatus U1.

Moreover, in experimental example 1, after each set is carried out, motions of a subject are classified at said initial values without carrying out connection weight learning processing (refer ST14 of FIG. 9).

Furthermore, in experimental example 1, when an output element group $G_\gamma^3$ (i=1, 2, . . . , 6) having more than three firing elements at consecutive three time frames has been detected, in company with classification of motion type and velocity corresponding to said output element group $G_\gamma^3$, following to calculation of said classification value $d_\gamma(p_\gamma)$ ($\gamma$=1, 2, . . . , 6, p$\gamma$=1, 2, . . . , Ps) of said output element group $G_\gamma^3$ at consecutive twelve time frames after motion classification, the average $d_\gamma$ of said classification value $d_\gamma(p_\gamma)$ within the total 15 time frame is calculated and then smoothed. That is to say, in example 1, the average $d_\gamma$ is calculated within a specific time frame when classification value $d_\gamma(p_\gamma)$ other than 0 is obtained from start of motion classification to the end of the fifteenth time frame.

Furthermore, in experimental example 1, if 0 is output consecutively for ten time frames after motion classification starts, it is determined as the end of motion classification.

(Regarding Classification Rate DR(m) of Motion Types)

Classification rate stands for the value when any of the six motions is actually carried out, the total frame number when the actually performed motion is correctly detected, divided by the total frame number when any of the six motions is detected. For instance, the classification rate of ⌈wrist flexion⌋ is the total frame number when more than three elements fire in said first output element group $G_1^3$ at consecutive three time frames, divided by the total frame number during the two second when output element group $G_\gamma^3$ ($\gamma$=1, 2, . . . , 6) having more than three elements firing elements is detected when ⌈wrist flexion⌋ is performed.

Accordingly, during the two seconds when a specific motion is performed, let the total frame number of correctly detected said specific motion be $f_m$ (m=1, 2, . . . , 6), the total frame number for any of the motion other than said specific motion be $f_{m''}$ (m≠m'', m''=1, 2, . . . , 6), if the classification rate of said specific motion is represented by DR(m) (m=1, 2, . . . , 6), the classification rate of said specific motion DR(m) [%] can be expressed by the following equation (21).

$$DR(m) = f_m / (f_m + f_{m\square}) \times 100 \qquad (21)$$

Regarding Classification Rate DRsp(m) of Motion Velocities)

The classification rate DRsp(m) of motion velocities is the average of the value indicating that, when any of the 18 motions are actually performed, the degree to which the classification value $d_\gamma(p_\gamma)$ ($\gamma$=1, 2, . . . , 6, p$_\gamma$=1, 2, . . . , Ps) of the output element group $G_\gamma^3$ (i=1, 2, . . . , 6) having more than three elements firing elements, approximates the classification value corresponding to said actual motion, namely classification value corresponding to the five patterns which are regarded as said correspondence relationship information T, namely any of the five values (2.5), (3.5), (4.5), (5.5), (6.5), a target value, over the overall frame number Ps. More specific, said classification value $d_\gamma(p_\gamma)$ is the average of a value, wherein it is 0[%] when it detaches from the classification value corresponding to the actual 18 motions by more than 4, and 100 [%] when it is in full accordance, over the overall frame number Ps. For instance, if the classification value based on said correspondence relationship information T is 2.5 when the motion ⌈wrist flexion⌋ is actually performed at velocity mode ⌈fast⌋, the motion classification rate of ⌈wrist flexion⌋ is 80% if each of the classification values of said first output element group $G_1^3$, $d_1(1)$~$d_1(ps)$ is 3.3 ($d_1(1)$=3.3) ({1−(2.5−3.3)/4}×100=80[%]).

As a result, when a specific motion is performed at any of the three velocities during two seconds, if $pd_\gamma(p_\gamma)$ ($\gamma$=1, 2, . . . , 6, $p_\gamma$=1, 2, . . . , Ps) represents the classification value per frame corresponding to said specific motion (any of the five correct classification values from 2.5 to 6.5), $DR_{sp}(m)$ represents the classification rate of velocities of said specific motion, the classification rate of said specific motion velocity $DR_{sp}$ (m) [%] can be expressed by the following equation (22).

$$DR_{sp}(m) = [\{4 - (pd_\gamma(1) - d_\gamma(1))\}/4 \times 100 + \{4 - (pd_\gamma(2) - d_\gamma(2))\}/4 \times 100 + \ldots + \{4 - (pd_\gamma(Ps) - d_\gamma(Ps))\}/4 \times 100]/(f_m + f_{m''}) \qquad (22)$$

(Experimental Results)

The experimental results are described as follows.

Figure 11:
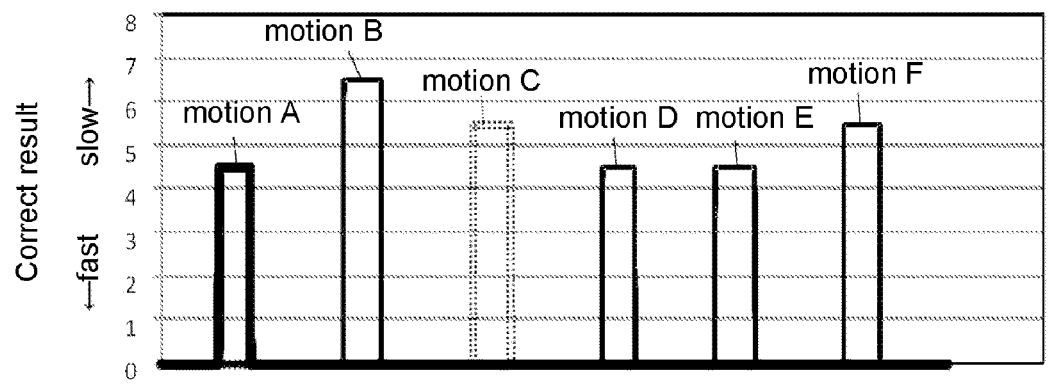
FIG. 11 illustrates the experimental results in experiment 1, wherein vertical axis is classification value and the horizontal axis is time [s]; indicating the classification values when the six motions from ┌motion A┘ to ┌motion A┘, among one set of the 18 motions, are actually performed by a subject at an interval of two seconds.
Figure 11:
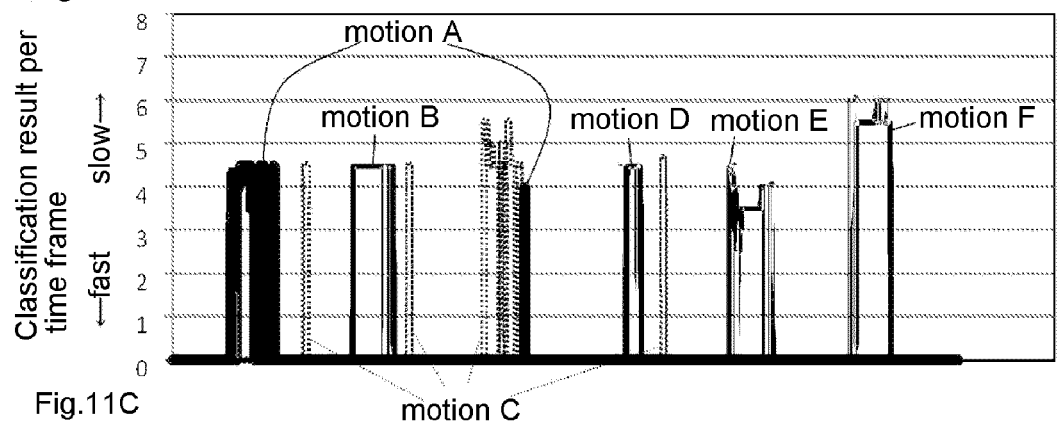
Figure 11:
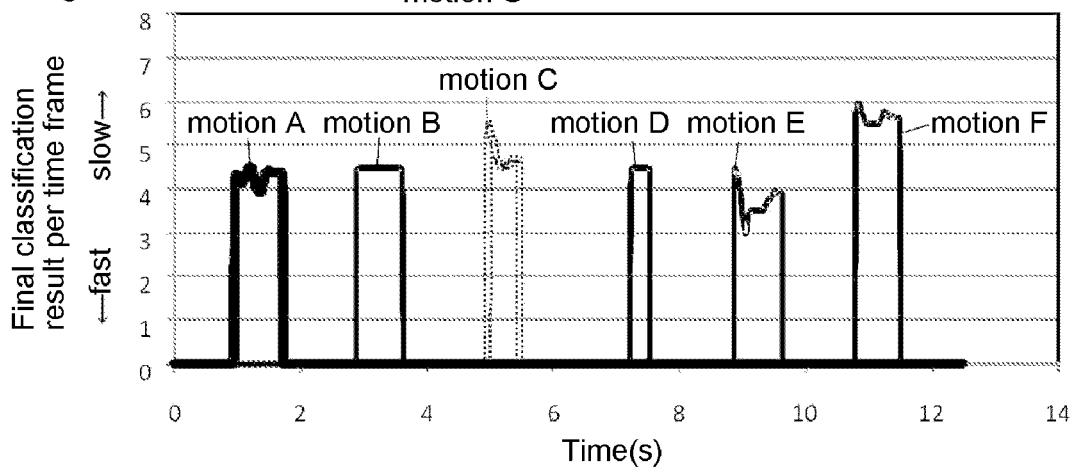

FIG. 11 illustrates the experimental results in experiment 1, wherein vertical axis is classification value and the horizontal axis is time [s]; indicating the classification values when the six motions from ⌈motion A⌋ to ⌈motion F⌋, among one set of the 18 motions, are actually performed by a subject at an interval of two seconds; FIG. 11A illustrates the correct classification values for six motions that are actually performed; FIG. 11B indicates the unsmoothed measured classification values for six motions that are actually performed against time frame; FIG. 11C illustrates the smoothed measured classification values for six motions that are actually performed against time frame.

Firstly, with regard to classification of motion type in experimental 1, namely the location and width of a graph, as shown in FIG. 11, it is understood that the graph of correct classification (refer to FIG. 11A) values can be roughly distinguished from that of the measured values (refer to FIG. 11B, FIG. 11C).

Besides, as shown in FIG. 11B, it can be seen, on a per frame basis, that ⌈motion A⌋ is mistakenly classified as being located right after ⌈motion C⌋ (refer to bold line in FIG. 11B), and ⌈motion C⌋ can be mistakenly classified as being located dispersedly between ⌈motion A⌋ and ⌈motion B⌋, after ⌈motion B⌋, and right after ⌈motion C⌋ (refer to dot line in FIG. 11B). Nevertheless, as shown in FIG. 11C, since the mistakenly classified ⌈motion A⌋ as well as ⌈motion C⌋ is instantaneous as less than 15 frame, namely 150 [ms](10×15=150 [ms]), it disappeared after being smoothed within 15 frames.

In addition, with regard to the classification of motion velocities in experimental example 1, namely height of graph, as shown in FIG. 11, it can be seen that five motions other than ⌈motion B⌋ can be roughly classified.

Figure 12:
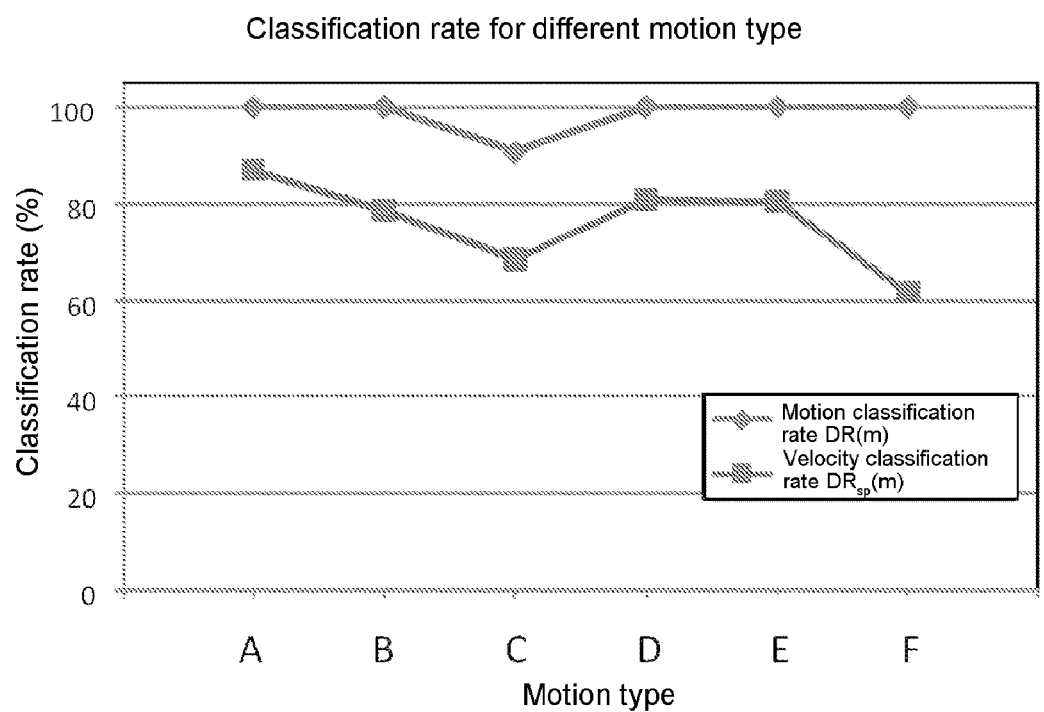
FIG. 12 is a line graph illustrating the experimental result in experimental example 1. wherein vertical axis represents classification rate [%] and the horizontal axis represents motion types; it illustrates the classification rates for six types of motions as well as the classification rate at three velocities for each motion when the six sets of all eighteen motions are actually performed.

FIG. 12 is a line graph illustrating the experimental results in experimental example 1, wherein vertical axis represents classification rate [%] and the horizontal axis represents motion types; it illustrates the classification rates for six types of motions as well as the classification rate at three velocities for each motion when six sets of all eighteen motions are actually performed.

In addition, as shown in FIG. 12, it can be seen that the classification rate DR(m) of six motions in experimental example 1 when six sets of all eighteen motions are actually performed is about 90[%] for ⌈motion C⌋ (DR(3)□90[%]), and approximately 100[%] for five motions other than ⌈motion C⌋ ⌈motion C⌋, ⌈motion B⌋, ⌈motion D⌋~⌈motion F⌋)(DR(m)=100[%])(m=1,2,4,5,6). In addition, the average classification rate for six motions is 98.42 [%]({DR(1)+ . . . +DR(6)}/6=98.42[%]).

Here, said average classification rate DR(m)98.42[%] does not mean that error occurred once or twice among 100 times of classification when six motions are performed, it shows whether the correct motion is classified or instantaneous error occurred during the period from start to end of motion classification processing (refer to FIG. 11)

Besides, said average classification rate $DR_{sp}(m)$ of three velocities of six motions is about 70[%] for ⌈motion C⌋, about 60[%] for ⌈motion F⌋ ($DR_{sp}$ (3)=70[%],$DR_{sp}$ (6)=60 [%]), and about 80[%] for four motions (⌈motion A⌋, ⌈motion B⌋, ⌈motion D⌋, ⌈motion E⌋) other than ⌈motion C⌋ and ⌈motion E⌋ ($DR_{sp}$ (m)=80[% (m=1, 2, 4, 5)]. In addition, the average $DR_{sp}(m)$ for three velocities of six motions is 76.15[%]({$DR_{sp}$ (1)+ . . . +$DR_{sp}$ (6)}/6=76.15 [%]).

Accordingly, it can be seen that, compared with the average classification rate for six motions (98.42[%]), the average classification rate $DR_{sp}(m)$ for three velocities of six motions (76.15[%]) is more than 20[%] lower. This is because the classification rate $DR_{sp}(m)$ for three velocities of six motions indicates the degree that said measured values of classification ($d_\gamma(1)$~$d_\gamma(15)$) approximate the ideal values ($pd_\gamma(1)$~$pd_\gamma(15)$) (refer to equation (22)), said measured values of classification ($d_\gamma(1)$~$d_\gamma(15)$) based on the values of eight elements of output element group $G_\gamma^3$ are not in full accordance with the ideal values ($pd_\gamma(1)$~$pd_\gamma(15)$).

Here in experimental example 1, before calculating said classification rate $DR_{sp}(m)$, the average $d_\gamma$ of said measured values of classification ($d_\gamma(1)$~$d_\gamma(15)$) over total fifteen frame is calculated and smoothed. As a result, said measured values of classification that are smoothed (average $d_\gamma$) tend to detach from said ideal values ($pd_\gamma(1)$~$pd_\gamma(15)$).

That is to say, even though a part of said measured values of classification ($d_\gamma(1)$~$d_\gamma(15)$) are in full accordance with said ideal values ($pd_\gamma(1)$~$pd_\gamma(15)$), if the rest of said measured values of classification ($d_\gamma(1)$~$d_\gamma(15)$) detach significantly from said ideal values ($pd_\gamma(1)$~$pd_\gamma(15)$), the average $d_7$ also detach from said ideal values ($pd_\gamma(1)$~$pd_\gamma(15)$). Consequently, said smoothing processing is presented as a reason causing discordance between said measured values of classification ($d_\gamma(1)$~$d_\gamma(15)$) and said ideal values ($pd_\gamma(1)$~$pd_\gamma(15)$), thus the average of said classification rate $DR_{sp}(m)$ (76.15[%]) for three velocities of six motions is more than 20[%] lower.

Figure 13:
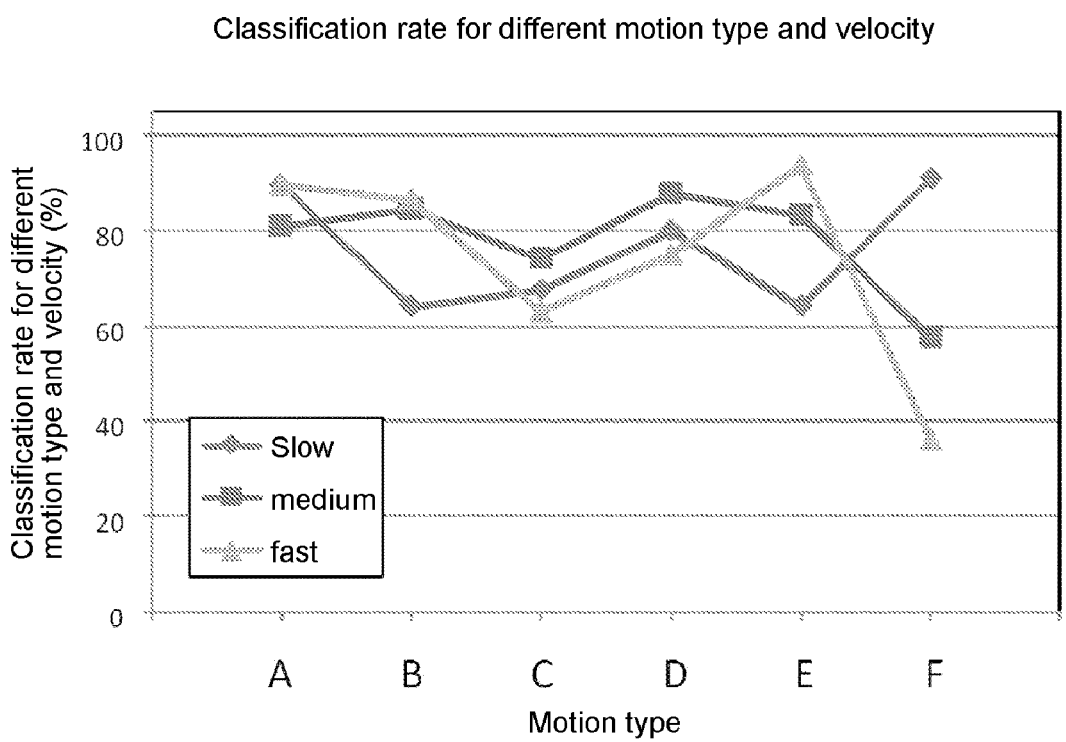
FIG. 13 is a line graph illustrating the experimental result in experiment 1. wherein vertical axis represents classification rate [%] of the motion velocity and the horizontal axis represents motion types; it illustrates the classification rates for six types of motions at three velocities for each motion when the six sets of all eighteen motions are actually performed.

FIG. 13 is a line graph illustrating the experimental result in experiment 1, wherein vertical axis represents classification rate [%] of the motion velocity and the horizontal axis represents motion types; it illustrates the classification rates for six types of motions at three velocities for each motion when the six sets of all eighteen motions are actually performed.

As shown in FIG. 13, the classification rate for three velocities of six motions is about 40[%] for ⌈motion F(fast)⌋, and in the range of about 60[%] to 90[%] for the seventeen motions other than ⌈motion F(fast)⌋. Moreover, the average of the classification rate for three velocities of six motions DRsp(m) is 74.12[%] for ⌈fast⌋, 78.30[%] for ⌈medium⌋, and 76.05[%] for ⌈slow⌋.

Figure 14:
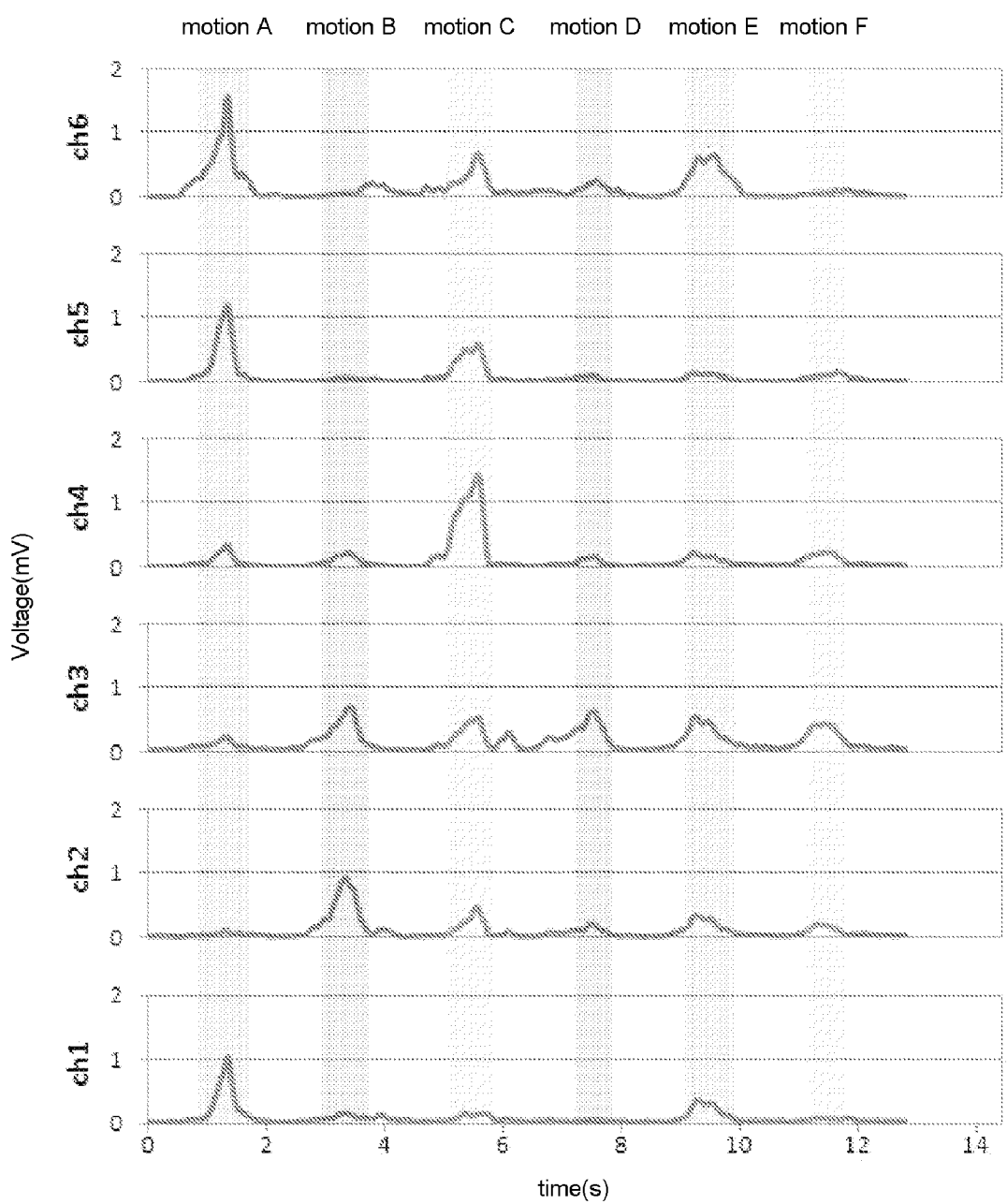
FIG. 14 illustrates the surface EMG measured from six channels of EMG sensor when six types of motions are actually performed in sequential order.

FIG. 14 illustrates the experimental results in experiment 1, wherein vertical axis represents voltage [mV] and the horizontal axis represents time [s]; it illustrates the surface EMG signals measured from six channels of EMG sensors when six types of motions are actually performed in sequential order.

As shown in FIG. 14, the surface EMG signals from 6 ch EMG sensors when ⌈motion F⌋ are actually performed are not striking except the maximum for 3 ch is 0.5[mV], the voltage values [mV] are comparatively lower compared with the surface EMG signals from 6 ch EMG sensors when other five motions are actually performed. Consequently, it is understood that the variation of input value over each frame is negligent when ⌈motion F(fast)⌋ is performed resulting extremely low classification rate [%] of about 40[%].

As a result, in order to improve classification rate [%], installation of additional new EMG sensors on other positions to obtain varied surface EMG signals are deemed effective when ⌈motion F⌋ is performed.

FIG. 15 illustrates the experimental results in experimental example 1 of the variation of time delay for estimation since building-up of a motion by the changing of classification rate with time; as shown in the table for different sets of motions, it indicates the change of classification rate at three velocities for six types of motions after a certain period time from the start of motion.

Figure 16:
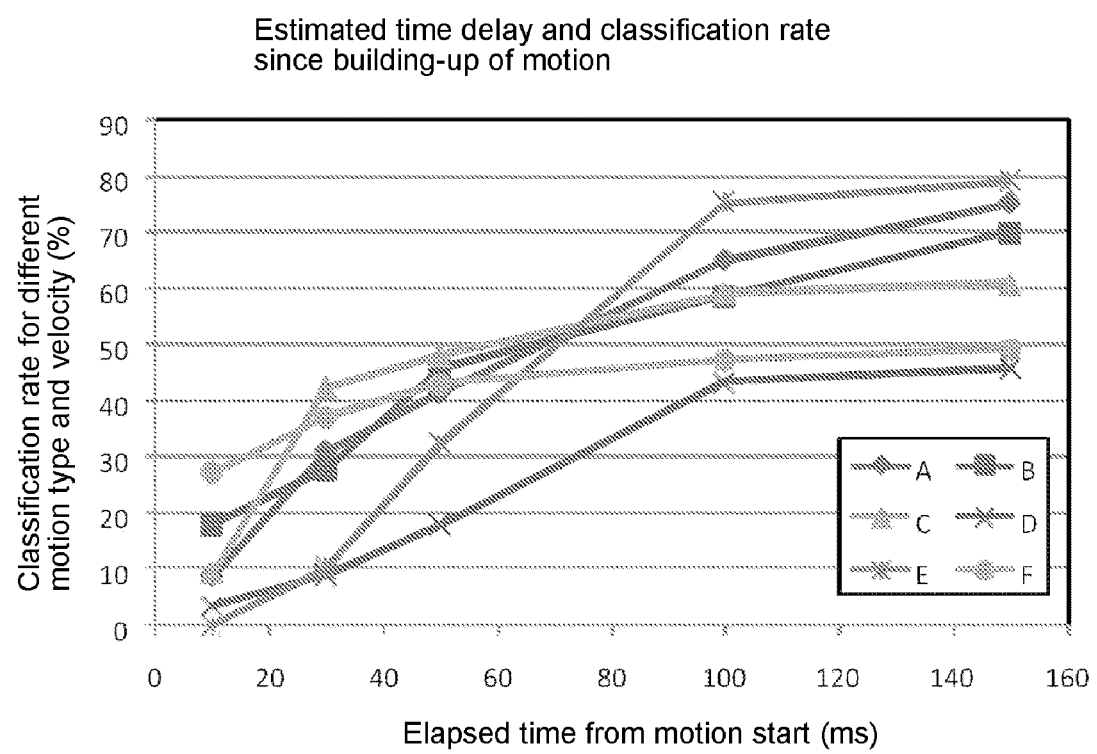
FIG. 16 illustrates the change of classification rate at three velocities for six types of motions after a certain period time from the start of motion based on the table in FIG. 15; wherein vertical axis is classification rate [%] and the horizontal axis is time [s].

FIG. 16 illustrates the change of classification rate at three velocities for six types of motions after a certain period time from the start of motion based on the table in FIG. 15; wherein vertical axis is classification rate [%] and the horizontal axis is time [s].

As shown in FIG. 15, FIG. 16, in experimental example 1, it is known that said classification rates $DR_{sp}(m)$ for three velocities of six motions when six sets are system S in experimental example 1, high classification rate can be achieved with little training as 36 sample data (two sets of 18 motions) of a subject.

Moreover, said surface EMG signals are detected 30 [ms] ~100 [ms] earlier than muscle contraction accompanying to actual motions of said subject. Accordingly, by means of said motion classification system S, classification is carried out almost simultaneously with start of muscle contraction accompanying to actual motions, namely, real-time classification, with classification rate for six motions of about 80 percent, whereas for 18 motions comprising six motions at three velocities of about 60 percent.

In addition, in experimental example 1, since classification rate increases with the increase of elapsed time since building-up of each motion, if classification result varies before and after a certain timing, there is high possibility that the varied classification result turns to be the correct classification result instead of the unvaried classification result. Therefore, for example, by means of said motion classification system S in experimental example 1, motion classification processing is proceeded after 18 motions being momentarily classified before muscle contraction, if there exists variation on classification result before and right after muscle contraction starts, once error is proved in said classification result before muscle contraction, classification rate for 18 motions can be improved by modifying classification result into said classification result after contraction start while maintaining real-time feature.

Furthermore, in experimental example 1, motion of a subject is classified by applying the initial values of said 60480 connection weight $\omega_{\gamma ij}^{\mu,\nu}$ as well as said 48 threshold values $h_i^\gamma$ without performing said connection weight training processing (refer to ST14 of FIG. 9). Consequently, as shown in embodiment 1, if said connection weight training processing is carried out to update said initial values, said 18 motions of a subject can be carried out with still higher classification rate at real time.

As a result, compared with non-patent literature 1 and 2 where motion classification based on said statistic approach requires training of initial values of connection weights, namely a large amount of training required for initial training in order to improve classification rate, said motion classification system S in embodiment 1 can reduce the amount of preparatory training required for initial training (number of provided samples). Accordingly, performed increase when the elapsed time period from the build-up time for each motion increases, e.g. 10 [ms], 30 [ms], 50 [ms], 100 [ms], 150 [ms] since start receiving EMG signals accompanying to each motion. That is to say, it is known that said classification rates $DR_{sp}(m)$ increase with elapsed shift time of 1, 3, 5, 10, 15 shift times.

Moreover, the average $DR_{sp}(m)$ of three velocities of six motions for each timing is 11.19[%] after 10 [ms], 26.31[%] after 30 [ms], 38.16[%] after 50 [ms], 58.16[%] after 100 [ms], and 63.40[%] after 150 [ms] since start of each motion.

Consequently, it can be seen that from 100 [ms] to 150 [ms] after start of each motion, the variation of average classification rates $DR_{sp}(m)$ tends to be gradual, and convergence on the increase of average classification rates $DR_{sp}(m)$ starts (refer to FIG. 14). In addition, the achievement level [%] to the upper limit 76.15[%] is 76.37[%] after 100 [ms] ((58.16)/(76.15)×100=76.37[%]), and 83.26[%] after 150 [ms] ((63.40)/(76.15)×100=83.26[%]) since start of each motion. As a result, it can be seen that after 100 [ms] since start of each motion, classification on three velocities of six motions has been almost achieved.

Here, as shown in FIG. 15, except for motions where $DR_{sp}(m)$ equals 0[%], the classification rate of motion type is 100[%]. Consequently, the classification rate DR(m) for each timing of six motions can be calculated to be 17.46[%] after 10 [ms], 39.68[%] after 30 [ms], 53.97[%] after 50 [ms], 80.16[%] after 100 [ms], and 88.09[%] after 150 [ms] since start of each motion. In addition, the achievement level [%] to the upper limit 98.42[%] is 81.45[%] after 100 [ms] ((80.16)/(98.42)×100=81.45[%]), and 89.42[%] after 150 [ms] ((88.09)/(98.42)×100=89.42[%]) since start of each motion.

As a result, as shown in experimental example 1, after 100 [ms] since start of each motion, classification can be achieved with classification rate for classification of motion types only of about 80 percent, whereas classification for motion types as well as velocities simultaneously of about 60 percent. That is to say, in experimental example 1, after 100 [ms] since start of each motion, classification is possible while classification rate on six motions of about 80 percent, whereas classification on 18 motions comprising six motions at three velocities of about 60 percent. Accordingly, with help of said motion classification said motion classification system S in embodiment 1, compared with non-patent literature 1 and 2, enables reduced preparatory training required for initial training (re-training) carried out when said subjects take turns for motion classification, thus reduces workload on said subject.

In addition, motions of said subject are classified by means of said selective desensitization neutral network with high training ability (generalization ability). Besides, eight input values $N_i(p)$, $N_a(p)$, $N_d(p)$ in embodiment 1 are calculated by removing noise (error, individual difference) from output signals (surface EMG signals) obtained from six EMG sensors SN1~SN6 (refer to ST104~ST106, equation (4) etc). Accordingly, said motion classification system S in embodiment 1 makes it easier for universally applicable setting of connection weights. As a result, motion classification of a subject can be achieved with high accuracy even if sampling is carried out on a third party other than the subject for initial training. That is to say, even if sampling is not carried out on the very person of said subject for initial training, motion classification of said subject can be achieved with high accuracy.

Besides, by means of said classification system S in embodiment 1, with regard to classification of six motions, high classification rate of 98.42[%] can be achieved, even if classification with real-time feature within 100 [ms] is required, high classification rate of more than 80[%] can be maintained therefore deems it practicable when classification time is concerned. In addition, with regard to classification of eighteen motions comprising six motions at three velocities, even without additional training, high classification rate of more than 76.15[%] can be maintained, and classification rate of more than 60[%] can be achieved even if classification with real-time feature within 100 [ms] is required.

Consequently, since no drastic increase for necessary training is required even for classification of numerous motions and velocities by means of classification system S in embodiment 1, compared with techniques described in non-patent literature 1 and 2 etc. where numerous training is further required corresponding to the increased motion types and velocities, motion classification of said subject can be carried out with little training.

Furthermore, there is no need to carry out complicated feature extraction processing with said classification system S in embodiment 1 to extract the features of increased motion types and velocities even with increased motion types and velocities for classification.

Accordingly, compared with techniques described in non-patent literature 1 and 2 etc. where said feature extraction processing in order for classification of numerous motions and velocities is complicated thus impair real-time feature, said classification system S in embodiment 1 is able to classify motion of a subject without impairing real-time feature.

As the result, said classification system S in embodiment 1 can carry out classification of (1) numerous motions, (2) together with estimation of velocity, (3) with high classification rate, (4) with little sample number required, (5) at real time.

Modified Embodiment

While the embodiment of the present invention has been illustrated and described in detail, as noted above, many changes can be made without departing from the spirit and scope of the invention described in the scope of claims. Accordingly, the scope of the invention is not limited by the disclosure of said embodiment. The modification examples of the present invention (H01~H017) are described as follows.

(H01) While six EMG sensors SN1~SN6 are applied (m=6) to classify six motions of a subject (m'=6, except ⌈neutral⌋) with the number determined as 30 (n=30) for elements of the input element group Gi1 of selective desensitization neutral network N as well as intermediate element group Gμ.ν2 respectively, and 8 (n'=8) for elements of output element group $G_\gamma^3$ in said embodiment, the values of m, n, m', n' are not limited to said embodiment, it is possible to make any change with the values. For example, in the case of classification of knee flexion, knee extension, two EMG sensors SN1, SN2 are applied (m=2) to classify two motions of a subject (m'=2, except ⌈neutral⌋) with the number determined as 10 (n=10) for elements of the input element group Gi1 of selective desensitization neutral network N as well as intermediate element group Gv.ν2 respectively, and 6 (n'=6) for elements of output element group Gγ3 for motion classification. That is to say, motions of less than 5 or more than 7 can be classified by applying EMG sensors of less than 5 or more than 7, or applying selective desensitization neutral network with random amount of elements in each layer from Na to Nb layers. Furthermore, even if more EMG sensors are applied to classify numerous motions, little training with high classification rate for each motion can be achieved by expanding said selective desensitization neutral network, wherein in contrast to increase of EMG sensors, the gradual increase of calculation amount leads to high generalization ability and high redundancy (because of strong resistance to addition of redundant variables).

(H02) In said embodiment, the integrated surface EMG signals (s1~s6) obtained from six EMG sensors SN1~SN6 are calculated by the control unit of said surface EMG measuring apparatus U1 and then sent to the computer unit H1 of said client PC for motion classification, and moreover, the integrated surface EMG signals (s1~s6) obtained from six EMG sensors SN1~SN6 can also be calculated by the control unit of the computer unit H1 of said client PC for motion classification. That is to say, said client PC for motion classification has functions prescribed in said surface EMG measuring apparatus U1, and production of a motion classification apparatus composed of said surface EMG measuring apparatus U1 and said client PC for motion classification integrally (U1+PC) is possible.

(H03) In said embodiment, in order to calculate said six average integrated values ($v_1$~$v_6$)(refer to equations (2-1),(2-1)), the time frame for each frame is set as 15 [ms] with said shift time as 10 [ms], but without limitation, said time frame as well as said shift time can be determined randomly. In addition, if said time frame as well as said shift time is changed, classification rate DR(m), $DR_{sp}$(m) (m=1, 2, ..., 6) of motion types as well as motion velocities as shown in experimental example tends to be affected. Moreover, if said time frame as well as said shift time is too long, classification result tends to lag behind the actual motion. As a result, it is advisable to determine said time frame as well as said shift time corresponding to classification rate and real-time feature required by the processing for respective usage while considering the usage of processing which applies said classification result.

(H04) In said embodiment, on the basis of five patterns of said correspondence relationship information T (refer to equations (19-1)~(19-5)), classification is carried out for motions while more than three elements of said output element group $G_\gamma^3$ ($\gamma$=1, 2, ..., 6) fire consecutively beyond classification frame number Ps. But motion classification is not limited to this method, while, for instance, if said output element group $G_\gamma^3$ is in accordance with said five patterns even for one time frame, namely said output element group $G_\gamma^3$ with four elements fire consecutively (ajacent) is detected, motion classification is also possible. In addition, if more than three elements of said output element group $G_7^3$ fire consecutively beyond classification frame number Ps, motions classification, in which at least either two elements fire consecutively, or all the firing elements are continuous, is possible.

(H05) When a plurality of motions are performed simultaneously, namely, when compound motion is carried out, in spite of the fact that said compound motion was never trained, it is possible to classify the individual components of the compound motion with said motion classification system S in said embodiment. For instance, when hand grasps while wrist bends, a combined motion of ⌈wrist flexion⌋ and ⌈hand grasp⌋ can be classified. With training of said compound motion, motion classification of said compound motion with higher classification rate can be expected. Consequently, in said embodiment, when a plurality of said output element group $G_\gamma^3$ exist in which more than three elements fire consecutively beyond classification frame number Ps, it can be classified as that a plurality of corresponding motions are performed simultaneously, but without limitation, for instance, if it is not clear which one of the corresponding plural motions is performed, it can be classified as either ⌈not classified⌋ or maintain ⌈neutral⌋ state with out carrying out classification.

(H06) In said experimental example 1, classification rate DR(m), $DR_{sp}$(m) (m=1, 2, ..., 6) of motion type as well as motion velocity are measured with 36 sample data obtained from two sets of 18 motions (six motions at three velocities) are trained for initial training, but the number of sample data is not limited to the experimental sample, for example, when only six motions are classified, either sample data less than 35 can be trained for initial training, or beyond initial state, over 37 sample data can also be trained when classification for 18 motions with higher classification rate or for more motions as well as velocities are expected. In this case, considering practicability, the number of sample data is determined in order not to be deemed as burdensome to a subject for initial training.

(H07) In said embodiment, the classified start time, type as well as velocity of said subject are, as displayed on display segment 2a (refer FIG. 8) of said motion classification image 2, displayed real-time on display H2 of said classification client PC; and without limitation to this, for instance, based on the classified motion types as well as velocities of said subject, it can be applied to carry out real-time repetition of the classified motions as well as velocities with prosthetic arms and limbs (e.g. hand grasps for prosthetic hand and knee bends or extends for prosthetic knee), and to classify the sequential motions of a wearer (operator) who wears robot suits, and also operate motors supplying assistance for the classified motions. More specifically, by determining said specific motor which applies a torque on specific joints in order to perform the classified motions, namely by determining the plural driving motors comprising robot suits, real-time repetition of classified motions (for instance, lifting heavy objects) can be achieved on robot suits at a velocity higher than classification velocity (for example, 10[%]~40[%] higher) to assist a wearer (operator). Additionally, corresponding to classified motion types as well as velocities of said subject, images on display H2 of said classification client PC which is a virtual reality device can be updated in a real-time pattern.

(H08) In said embodiment, 18 motions comprising six motions at three velocities of said subject (19 motions including ⌈neutral⌋) are classified, whereas it is not limited to the present motion types as well as velocities. Additionally, for example, through addition of elements separately into said output element group $G_\gamma^3$ in order to classify motion acceleration, motion acceleration can be classified. In this case, not only motion types (type information) and velocities (velocity information), angles (angle information) as well as accelerations (acceleration information) can also be classified simultaneously.

(H09) In said embodiment, five patterns of correspondence relationship information T are determined according to six surface EMG signals obtained from six EMG sensors SN1~SN6 as well as 18 motions comprising six motions at three velocities (refer to equations (17), (18), (19-1)~(19-5), (20-1), (20-2) etc), without limitation to this determining method, for example, correspondence relationship information T can be determined more accurately based on analog values according to signals obtained from velocity sensors as well as acceleration sensors (wave form indicting change of values of velocity and acceleration with elapsed time) as velocity information of each motion. In this case, compared with the setting of 5 patterns of correspondence relationship information T based on surface EMG signal and 18 motions, the training efficiency of initial training can be expected to be improved with classification rate furthermore improved.

(H010) In said embodiment, eight input values $N_i(p)$, $N_a(p)$, $N_d(p)$ based on six surface EMG signals are input into the selective desensitization neutral network N to classify 18 motions comprising six motions at three velocities, whereas the input values are not limited to surface EMG signals, for example, input values based on signals obtained from velocity sensors as well as acceleration sensors can also be input in to the selective desensitization neutral network N. In this case, compared with the case when motion classification is carried out according to input values $N_i(p)$, $N_a(p)$, $N_d(p)$ based only on surface EMG signals, classification rate can be furthermore improved.

(H011) In said embodiment, with regard to the average $d_\gamma$ ($\gamma=1, 2, \ldots, 6$, $d_\gamma=\{d_\gamma(1)+d_\gamma(2)+\ldots+d_\gamma(2)\}/Ps$) of classification rate $d_\gamma(p_\gamma)$ of output element group $G_\gamma^3$ for each time frame corresponding to classified motions, if $2.5 \leq d_\gamma \leq 3.5$, it is classified as 「fast」, if $3.5 \leq d_\gamma \leq 5.5$, it is classified as 「medium」, and if $5.5 \leq d_\gamma \leq 6.5$, it is classified as 「slow」. With no limitation to this, the boundary value 「3.5」 to separate 「medium」 from 「fast」, and the boundary value 「5.5」 to separate 「medium」 from 「slow」 can be determined randomly. In addition, motion velocities are not classified into just three levels of 「fast」, 「medium」, and 「slow」, classification of two levels or four levels is also possible. For example, four level classification is possible in which it is classified as 「high speed」 if $2.5 \leq d_\gamma \leq 3.5$, 「slightly fast (medium and high speed)」 if $3.5 \leq d_\gamma \leq 4.5$, 「medium speed」 if $4.5 \leq d_\gamma \leq 5.5$ and 「low speed」 if $5.5 \leq d_\gamma \leq 6.5$. In addition, for example, the calculated velocities [m/s] corresponding to said average $d_\gamma$ can be classified whereas said average $d_\gamma$, which indicates velocity, can also be classified.

(H012) In said embodiment, the input values $N_a(p)$ based on the sum A I $EMG_{all}$ (p) of error eliminated value A I $EMG\epsilon_i$ (p) (p=1, 2, . . . ) are input into the values of elements, $x_1^8 \sim x_{30}^8$, of sum input element group $G_8^1$, with no limitation to the input values, for example, the norm (square root of sum of squares) of six error eliminated value A I $EMG\epsilon_i$ (p) can also be input as input value. Moreover, norm A I $EMG_{all}$ (p)' that substitutes sum A I $EMG_{all}$ (p) as input value can be expressed in the following equation (5)'.

$$AIEMG_{all}(p)' = \{(AIEMG_{\varepsilon_1}(p))^2 + (AIEMG_{\varepsilon_2}(p))^2 + \ldots + (AIEMG_{\varepsilon_6}(p))^2\}^{1/2} \quad \text{equation (5)'}$$

Besides, for example, input values based on integrated values of two pre-determined error eliminated value A I $EMG\epsilon_i$ (p) can also be input. In addition, the input value based on the integrated value obtained by subtracting the rest error eliminated values A I $EMG\epsilon_i$ (p) (i=1, 2, . . . ) from the first error eliminated value A I $EMG\epsilon_1$ (p) can also be input.

Furthermore, if said integrated value is A I $EMG_{dif}$(p)', the sum A I $EMG_{all}$ (p) that is substituted by said integrated value is A I $EMG_{dif}$ (p)' can be express in the following equation (5)".

$$AIEMG_{dif}(p)' = AIEMG_{\varepsilon_1}(p) - AIEMG_{\varepsilon_2}(p) - \ldots - AIEMG_{\varepsilon_6}(p) \quad \text{equation (5)"}$$

(H013) In said embodiment, the surface EMG signal, as one biosignal, is measured to classify motions of a subject, and with no limitation to this information, for example, brain wave can also be measured to classify motions of a subject as one biosignal.

(H014) In said embodiment, the sum input element group $G_8^1$ is taken as the element group for multiple desensitization (multiplex element group), but with no limitation, for example, any one or a plurality of the other input element groups $G_1^1 \sim G_7^1$ as well as intermediate element groups $G_{1.2}^2 \sim G_{7.6}^2$ can be taken as the element group for multiple desensitization. In addition, if a plurality of element groups $G_1^1 \sim G_8^1$, $G_{1.2}^2 \sim G_{7.6}^2$ are selected as the multiplex element group, the plural multiplex element group results in a multiple desensitization of over triple desensitization instead of double desensitization in embodiment. For example, if the sum input element group $G_8^1$ is selected as multiplex element group for double desensitization, whereas the integrated input element group $G_7^1$ is selected as multiplex element group for triple desensitization, by calculating the product of the doubly desensitized value of element of input element group $G_v$, $(x_i^\mu)$, $\{(x_i^\mu) \times (g_j^{\mu,v}) \times (g_k^{\mu,v,8})\}$ and the differential output sensitivity $(g_k^{\mu,v,7})$ aiming for triple desensitization, (k'=σ" (i), where k' is random number), $\{(x_i^\mu) \times (g_j^{\mu,v}) \times (g_k^{\mu,v,8}) \times (g_k^{\mu,v,7})\}$, triple desensitization can be carried out, and moreover, multiple desensitization beyond quadruple is likewise possible to be carried out.

(H015) In said embodiment, the product of the value of element of input element group $G_v$, $(x_i^\mu)$, and the value of output sensitivity $(g_j^{\mu,v})$, is calculated to carry out selective desensitization, then the product is multiplied by the value of sum output sensitivity $(g_k^{\mu,v,8})$, namely, $\{(x_i^\mu) \times (g_j^{\mu,v}) \times (g_k^{\mu,v,8})\}$, is calculated to carry out double desensitization, as shown in equation (13), while there is no limitation to the order of calculation, for example, double desensitization can also be carried out by first multiplying the value of element of input element group $G_v$, $(x_i^\mu)$, by the value of sum output sensitivity $(g_j^{\mu,v})$, $(x_i^\mu) \times (g_k^{\mu,v,8})$ to carry out selective desensitization, then multiplying the product by output sensitivity $g_j^{\mu,v}$ to calculate $(x_i^\mu) \times (g_k^{\mu,v,8}) \times (g_j^{\mu,v})$; or double desensitization can also be carried out multiplying the value of element of input element group $G_v$, $(x_i^\mu)$, by the product of output sensitivity $g_j^{\mu,v}$ and sum output sensitivity $(g_k^{\mu,v,8})$ $(g_j^{\mu,v}) \times (g_k^{\mu,v,8})$ to calculate $(x_i^\mu) \times (g_j^{\mu,v}) \times (g_k^{\mu,v,8})$, or double desensitization can also be carried out by multiplying simultaneously the product of the value of element of input element group $G_v$, $(x_i^\mu)$, output sensitivity $g_j^{\mu,v}$ and sum output sensitivity $(g_k\mu.v,8)$ to calculate $(x_i^\mu) \times (g_j^{\mu,v}) \times (g_k^{\mu,v,8})$.

(H016) With the motion classification system S of said embodiment, surface EMG signals are measured to classify motions of a subject, but there is no limitation to its application, for example, motion type and velocity of a lost limb of a disabled person can also be estimated. More specifically, with regard to a subject who has a lost hand, as described in embodiment 1, since surface EMG signals vary with operational decision of said subject, by measuring the surface EMG signals obtained from said six EMG sensors SN1~SN6 attached on said six positions on forearm of said subject, it is possible to estimate motion type and velocity that the subject intends to perform with the lost hand, therefore enable estimation of operational decision of a subject even when no actual motion is performed with the lost hand.

(H017) With the motion classification system S of said embodiment, motions of a subject are classified according to the measured surface EMG signals, but classification estimating system is not limited by disclosure of said embodiment, for example, it is possible to estimate motions of a person or an animal by taking video signals, to estimate operational decision of a static person, animal or plant by measuring brain wave signals, to estimate the state of abiotic objects by measuring temperature and humidity, to estimate climate and natural phenomenon by measuring temperature and humidity, to estimate the price of real estate by collecting information such as location etc, and to estimate exchange rate and stock price by collecting information such as economic index•financial policy etc. That is to say, it is possible to estimate all sorts of events from extracted information. More specifically, similar to embodiment 1, the average integrated values $(v_i)$ of integrated values $(s_i)$ of said each information (video signal, brain wave signal, temperature•humidity, location, economy index•financial index etc), as a wave form signal whose value changes over time, are calculated for each shift time, the sum of said average integrated values $(v_i)$ and the differential value of said sum at each time frame are calculated (refer to equations (5), (6)), and the by calculating the input values $(N_t(p), N_a(p), N_d(p))$ based on average integrated values•differential values and sum (refer to equations (7-1)~(8-3)), similar to surface EMG signals, the input values $(N_t(p), N_a(p), N_d(p))$ can be input into said selective desensitization neutral network N (refer to FIG. 5) which enables multiplex desensitization, and all sorts of events (motion, intention, state, climate and natural phenomena, real estate price, exchange rate and stock price) can be estimated.

INDUSTRIAL APPLICABILITY

By means of said motion classification system S as well as said motion classification program AP1 of the present invention, classified motions and velocities can be performed for real-time repetition with prothetic hands and limbs to assist general motions of a lost limb of a disabled person, or it can be applied to provide power assistance to operators (laborers) with heavy load in which motions of said operators who wears robot suits are classified in order to activate motors for power assistance for classified motions, or even applied for control of virtual reality devices such as sensory games and other interface devices.

What is claimed is:
1. A classification estimating system for a subject's motion, based on a multi-layered neural network comprising:
a first measuring device configured to measure first information as a first biosignal according to a first measuring section of the subject;
a second measuring device configured to measure second information as a second biosignal according to a second measuring section of the subject;
a computer-readable memory storing executable instructions; and
a processor in communication with the computer-readable memory and the first and second measuring devices, wherein the processor is programmed by the executable instructions to at least:
use the multi-layered neural network, the multi-layered neural network comprising an input element group in an input layer of the multi-layered neural network, an intermediate element group in a hidden layer of the multi-layered neural network and an output element group in an output layer of the multi-layered neural network, for estimating an action of the subject;
wherein the input element group of the multi-layered neural network comprises a first input element group and a second input element group, the first element group comprising a first plurality of input elements, the second element group comprising a second plurality of input elements;
determine values of a first input variable based on the first information;
provide each value of the first input variable to each of the first plurality of input elements of the first input element group;
determine values of a second input variable based on the second information;
provide each value of the second input variable to each of the second plurality of input elements of the second input element group;
wherein the intermediate element group of the multi-layered neural network comprises a first intermediate element group, the first intermediate element group comprising a plurality of intermediate elements;
set values of a first output sensitivity according to each value of each input element of the second input element group in order for some values of a first intermediate variable to become zero, and the remaining values of the first intermediate variable to become discrete values other than zero;
set values of a first multiplex output sensitivity according to each value of each element of a multiplex input element group in order for some values of the first intermediate variable to become zero, and the remaining values of the first intermediate variable to become discrete values other than zero;
determine the first intermediate variable based upon a product of each value of input element of the first input element group, a value of the first output sensitivity, and the first multiplex output sensitivity such that the first intermediate variable is equal to zero when either the value of the first output sensitivity or the first multiplex output sensitivity is set equal to zero;
wherein the output element group of the multi-layered neural network comprises a plurality of output elements;
determine each output element based upon a value of output variables which is a product of said each value of intermediate element of the intermediate element group and a connection weight, wherein the values of output variables are zero or other than zero;
wherein the connection weight corresponds to an importance of values of the intermediate elements;
store correspondence relationship information that specifies a correspondence relationship between a plurality of classification information in order to classify an action of the subject, and a combination pattern of the values of said plurality of output elements which comprise discrete values of zero or discrete values other than zero;
estimate said classification information for the subject's motion and information according to said first and second information based on said correspondence relationship information and the combination pattern of values of said plurality of output variables; and
display the classification information.
2. A classification estimating system according to claim 1:
wherein said intermediate element group of the multi-layered neural network further comprises a second intermediate element group comprising a plurality of intermediate elements;
wherein said processor is further programmed by the executable instructions to:
set values of a second output sensitivity according to each value of each input element of the first input element group;

set values of a second multiplex output sensitivity according to each value of each element of a multiplex input element group;

determine a second intermediate variable based upon a product of each value of input element of the second input element group, a value of the second output sensitivity, and the second multiplex output sensitivity such that the second intermediate variable is equal to zero when either the value of the second output sensitivity or the second multiplex output sensitivity is set equal to zero; and calculate said output element group based upon the values of output variables, wherein the output variables are calculated based upon each value of the elements of said intermediate variables and each value of connection weights corresponding to the importance of each value of said immediate elements.

3. A classification estimating system according to claim 1, wherein said processor is further programmed by the executable instructions to:

update each value of said connection weights based on a difference from real classification information extracted from said input first and second information when estimating said classification.

4. A classification estimating system according to claim 1, wherein said processor is further programmed by the executable instructions to:

calculate each value of each element of said multiplex element group according to said first and second information.

5. A classification estimating system according to claim 4, further comprising:

measuring devices comprising said first measuring device which measures said surface EMG signals at said first measuring section arranged on said skin; and said second measuring device which measures said surface EMG signals at said second measuring section arranged on said skin, wherein among the EMG signals indicating the information on potential change based on said operational decision, said EMG signals measured at the skin of said subject are taken as said surface EMG signals, whereas said EMG signals are taken as the surface EMG signals;

wherein said processor is further programmed by the executable instructions to:

calculate integrated values of said surface EMG signals measured by said first measuring device as the first integrated value, as well as the integrated values of said surface EMG signals measured by said second measuring device as the second integrated values;

calculate average values of the first integrated values as the first average integrated values over a certain preset shift time, as well as the average values of the second integrated values as the second average integrated value over said shift time within a certain preset time frame;

wherein said input element group comprises said first input element group into which are input the values of said first input variable over said shift time according to said first average integrated value, and said second input element group into which are input the values of said second input variable over said shift time according to said second average integrated value, wherein said first information is taken as said first average integrated value and said second information is taken as said second average integrated value.

6. A classification estimating system according to claim 4, wherein said processor is further programmed by the executable instructions to:

estimate said classification information including, information on types as well as information on force as the information of force of said motions.

7. A classification estimating system according to claim 6, wherein said processor is further programmed by the executable instructions to:

estimate said classification information comprising velocity information associated with said motion, based on said force information on types to specify the information of motion types according to said operational decision, and the information on force as the information of force of said motions.

8. A classification estimating system according to claim 7, wherein:

said output element group further comprises a second output element group comprising of a plurality of output elements into which are input values of second output variables corresponding to a second operational decision among the values of said output variables;

wherein said processor is further programmed by the executable instructions to:

store said correspondence relationship information which specifies the correspondence relationship between said information on types of said first operational decision as well as said velocity information, and the value of said first output variables; and the correspondence relationship between said information on types of said second operational decision as well as said velocity information, and the value of said second output variables;

estimate said type information of said classification information as well as said velocity information according to said first and second information into which are input the values based on said correspondence relationship information as well as the calculated values of said first output variables and said second output variables; and indicate said type information of said classification information, as well as said velocity information.

9. A classification estimating system for a subject's motion comprising:

an input value memorizing unit adapted to memorize variables of a multi-layered neural network comprising an input element group in an input layer of the multi-layered neural network, an intermediate element group in an intermediate layer of the multi-layered neural network, and an output element group in an output layer of the multi-layered neural network;

an intermediate value calculating unit adapted to calculate values of first intermediate variables based on input values stored in the input memorizing unit;

an output calculating unit adapted to calculate values of output variables based on the first intermediate variables;

a classification information estimating unit adapted to estimate classification information based on classified information of an activity of the subject, and further adapted to provide correspondence relationship information associated with a correspondence relationship between said value of output variables, and said value of output variables calculated by said value of output calculating unit;

a classification information display unit adapted to display said classification information estimated according to said classification information estimating unit, wherein the input element group comprises a first input element group and a second input element group, the first element group comprising a plurality of first input elements, the second element group comprising a plurality of second input elements;

a first measuring device adapted to measure first information as a biosignal according to a first measuring section of the subject;

a processor programmed by executable instructions to:

determine values of a first input variable based on the first information;

provide each value of the first input variable to each first input element of the first input element group;

a second measuring device adapted to measure second information as a biosignal according to a second measuring section of the subject;

wherein the processor is further programmed by the executable instructions to:

determine values of a second input variable based on the second information;

provide each value of the second input variable to each second input element of the second input element group;

wherein the intermediate element group comprises a first intermediate element group;

wherein the first intermediate element group comprises a plurality of intermediate elements;

wherein the processor is further programmed by the executable instructions to:

set values of a first output sensitivity according to each value of input element of the second input element group in order for some values of a first intermediate variable to become zero, and the remaining values of the first intermediate variable to become discrete values other than zero;

set values of a first multiplex output sensitivity according to each value of element of a pre-set multiplex input element group in order for some values of the first intermediate variable to become zero, and the remaining values of the first intermediate variable to become discrete values other than zero; and determine the first intermediate variable based upon a product of each value of input element of the first input element group, a value of the first output sensitivity, and the first multiplex output sensitivity such that the first intermediate variable is equal to zero when either the value of the first output sensitivity or the first multiplex output sensitivity is set equal to zero;

wherein the output element group of the multi-layer neural network comprises a plurality of output elements;

wherein each output element input by the value of output variables which is a product of said each value of intermediate element of the intermediate element group and a connection weight, wherein the values of output variables are zero or other than zero;

wherein the connection weights correspond to importance of values of the intermediate elements;

a correspondence relationship information memorizing unit adapted to memorize correspondence relationship information, which specifies a correspondence relationship between a plurality of classification information in order to classify an action of the subject, and the combination pattern of the value of said a plurality of output elements which comprise an output element group are zero or discrete values other than zero;

wherein said classification information for the subject's motion and information according to said first and second information estimated by the classification information estimating unit adapted to estimate based on said correspondence relationship information pre-stored in said correspondence relationship memorizing unit and the calculated combination pattern of values of said plurality of output variables are zero or discrete values other than zero.

\* \* \* \* \*